United States Patent
Garst et al.

(10) Patent No.: US 7,919,630 B2
(45) Date of Patent: Apr. 5, 2011

(54) SYNTHESIS OF IMIDAZOLE 2-THIONES VIA THIOHYDANTOINS

(75) Inventors: Michael E. Garst, Newport Beach, CA (US); Lloyd J. Dolby, Eugene, OR (US); Shervin Esfandiari, Eugene, OR (US); Alfred A. Avey, Jr., Eugene, OR (US); Vivian Rose MacKenzie, Eugene, OR (US); Charles David Muchmore, Eugene, OR (US)

(73) Assignee: Allergan, Inc., Irvine, CA (US)

( * ) Notice: Subject to any disclaimer, the term of this patent is extended or adjusted under 35 U.S.C. 154(b) by 493 days.

(21) Appl. No.: 11/468,187

(22) Filed: Aug. 29, 2006

(65) Prior Publication Data

US 2007/0203344 A1 Aug. 30, 2007

Related U.S. Application Data

(60) Provisional application No. 60/722,743, filed on Sep. 30, 2005.

(51) Int. Cl.
*C07D 233/84* (2006.01)
*C07D 233/86* (2006.01)

(52) U.S. Cl. .................................................. 548/325.1
(58) Field of Classification Search ................ 548/325.1
See application file for complete search history.

(56) References Cited

OTHER PUBLICATIONS

Koltai et al., Chemische Berichte (1971), 104(1), pp. 290-300.*
Jackman, et al. "The Preparation of Some Substituted Thiohydantoins and Thioimidazoles," Journal of the American Chemical Society, American Chemical Society, Washington, DC, US, vol. 70, 1948, pp. 2884-2886, XP000992597.
Nyitrai, et al., "Hydantoins, Thiohydantoins and Glycocyamidines, XXVII, reductive rearrangements of the retrobenzylic acid type induced by Lewis acid, IV, scope of the aluminium chloride induced reactions of dithiohydantoins with arenes," ACTA Chimica Academiae Scientiarum Hungaricae, vol. 60, No. 1-2, 1969, pp. 141-149, XP009080567.

* cited by examiner

*Primary Examiner* — Laura L. Stockton
(74) *Attorney, Agent, or Firm* — Kevin J. Forrestal; John E. Wurst; Doina G. Ene

(57) ABSTRACT

The present invention provides a method of making an imidazole 2-thione which comprises the step(s) of reducing a thiohydantoin to said imidazole-2-thione.

8 Claims, 1 Drawing Sheet

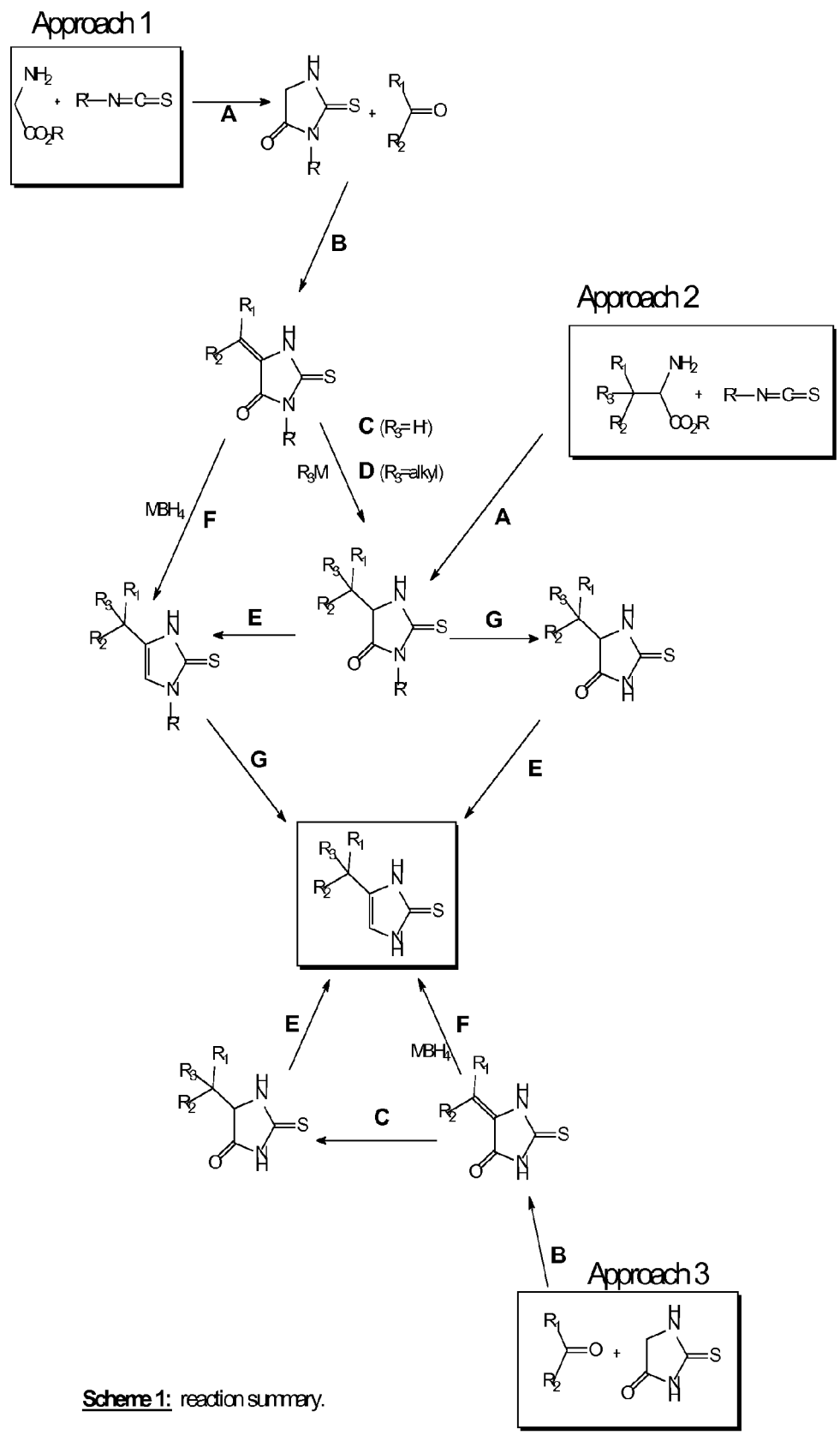
Scheme 1: reaction summary.

SYNTHESIS OF IMIDAZOLE 2-THIONES VIA THIOHYDANTOINS

CROSS REFERENCE TO RELATED APPLICATIONS

This application is based on, and claims the benefit of, U.S. Provisional Application No. 60/722,743 filed Sep. 30, 2005, and which is incorporated herein by reference.

BACKGROUND OF THE INVENTION

Field of the Invention

The present invention relates to 4-substituted 2-thio imidazoles having pharmaceutical activity or useful as intermediates in the preparation of pharmaceutical products.

BRIEF SUMMARY OF THE INVENTION

This present invention provides a method of preparation of 4-substituted 2-thioimidazoles. In particular, the present invention provides a method for generating a chiral carbon at the α-position.

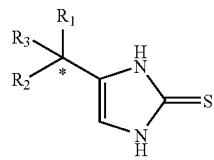

4-substituted 2-thio imidazoles are useful as pharmaceutical products and as intermediates for preparing pharmaceutical products.

BRIEF DESCRIPTION OF THE DRAWING

The Drawing FIGURE describes three approaches for making the thiohydantoins of this invention. The reactions involved in these approaches are designated as A through G.

DETAILED DESCRIPTION OF THE INVENTION

In one embodiment of the present invention, (Approach 2 in Scheme 1) an optically active amino acid or derivative is

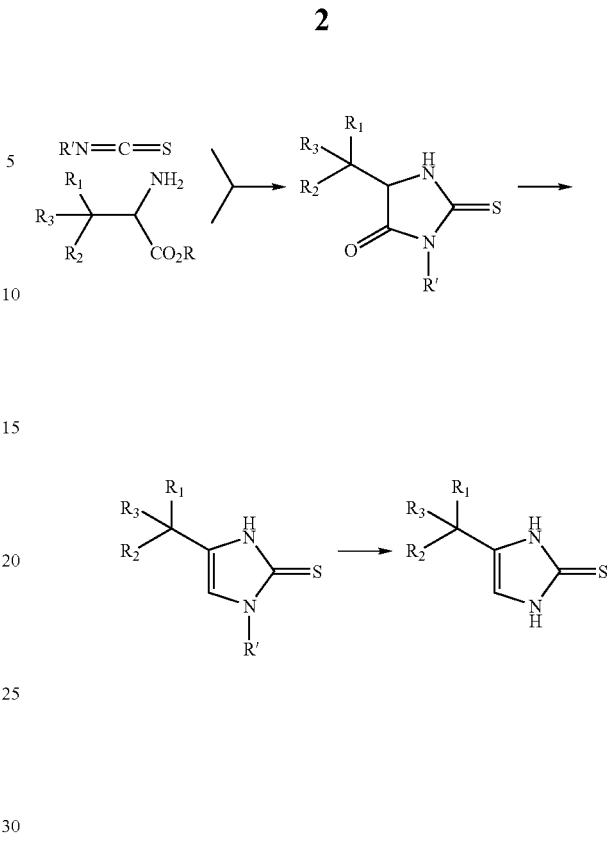

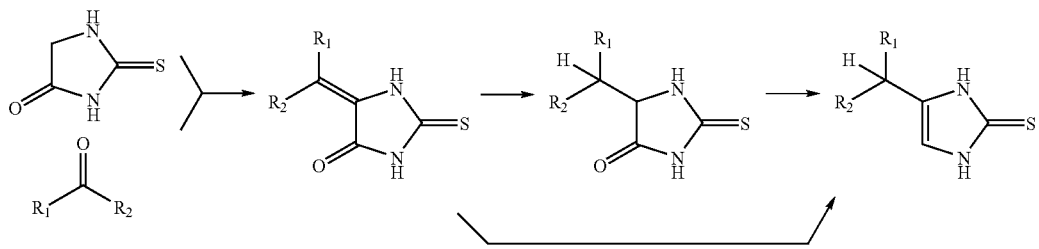

used to prepare the optically-active 4-substituted 2-thio imidazole. The chirality would be preserved on reaction with isothiocyanates to form 3-substituted thiohydantoins (Reaction A). The thiohydantoins can be reduced to the 3,5-disubstituted imidazolethiones. Deblocking the nitrogen results in formation of the desired chiral 5-substituted imidazolethione (3-steps A, E, G).

The allyl isothiocyanate starting materials are readily available articles of commerce.

One alternative embodiment of the method of the present invention, (Approach 3 in Scheme 1) introduces a 5-substituent directly into thiohydantoin itself. This is done by condensation with carbonyl compounds to form alkylidene and arylidene thiohydantoins (Reaction B). We have discovered that these thiohydantoins can be reduced either to a final product (Reaction F) or to an intermediate thiohydantoin that could be further reduced (Reactions C, E). A potential point for introduction of chirality is in the 1,4-addition of hydride (Reaction C).

An additional embodiment of the present invention (Approach 1 in scheme 1) would extend to 1,4-addition to use of metal alkyls (or aryls) (Reactions C, D), for the introduction of chirality. We have found that these reactions require that the 3-nitrogen of the alkylidene or arylidene thiohydantoins be protected. Again, these protected species are prepared from an amino acid (glycine) and in isothiocyanate. It has been found that the reductions (reaction F) shown above are also easier with the protected thiohydantoins ($R_3=H$).

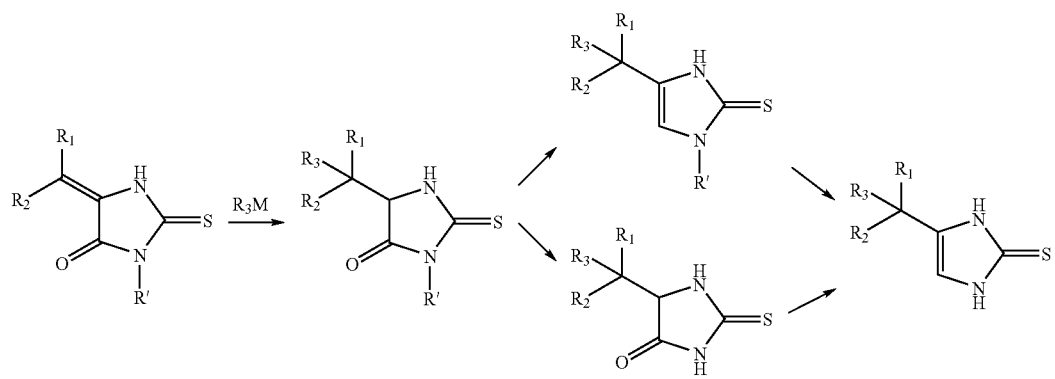

The reaction steps of the present invention, which are designated as A-F are discussed below.

Reaction A. Formation of thiohydantoins by the reaction of amino acids and derivatives with isothiocyanates

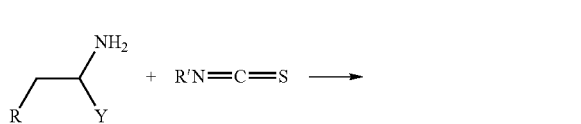

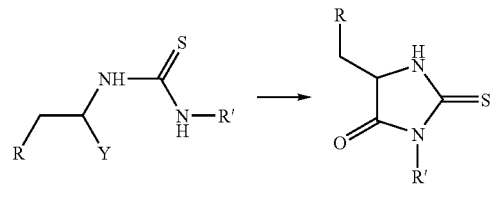

The use of aqueous pyridine as solvent is satisfactory for formation of the intermediate thiourea. It is also possible, using amino acid esters, to carry out this reaction in dichloromethane. This offers a more facile work-up. While closure to the thiohydantoin generally only required heating with aqueous acid, cyclization may require a strong base, such as sodium hydride if the protecting group is t-butyl.

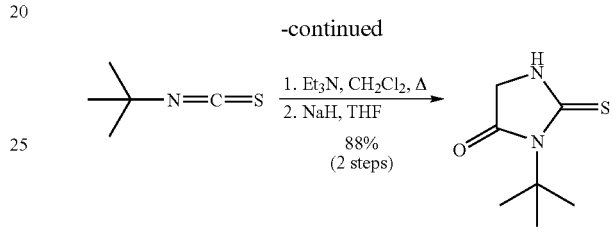

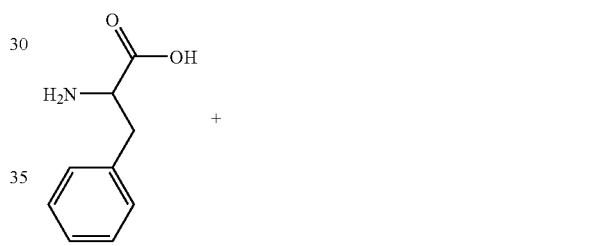

-continued

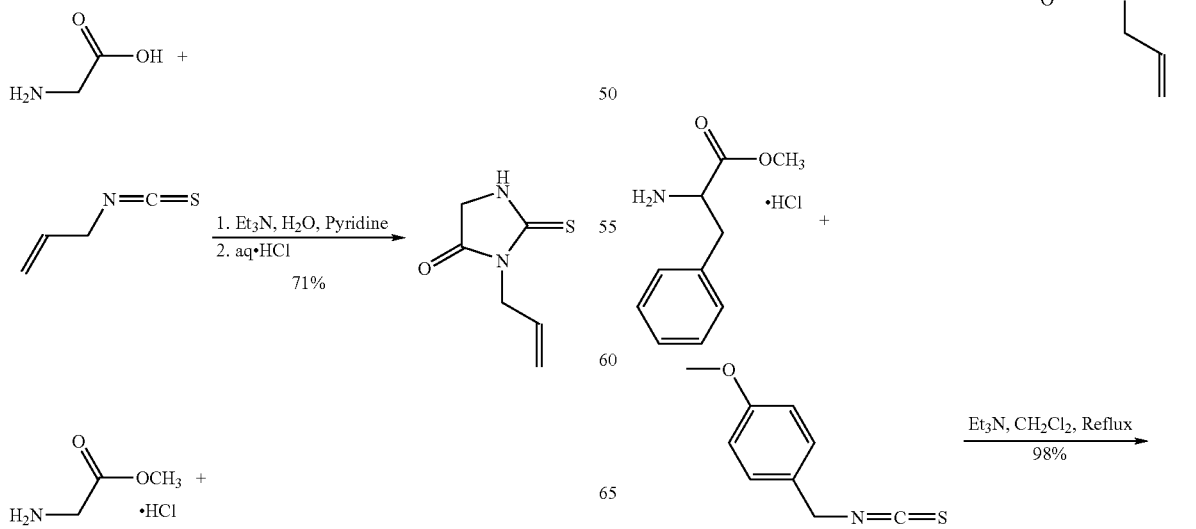

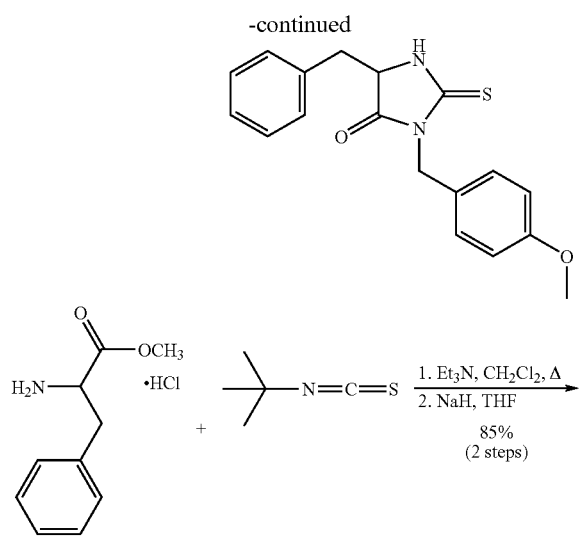
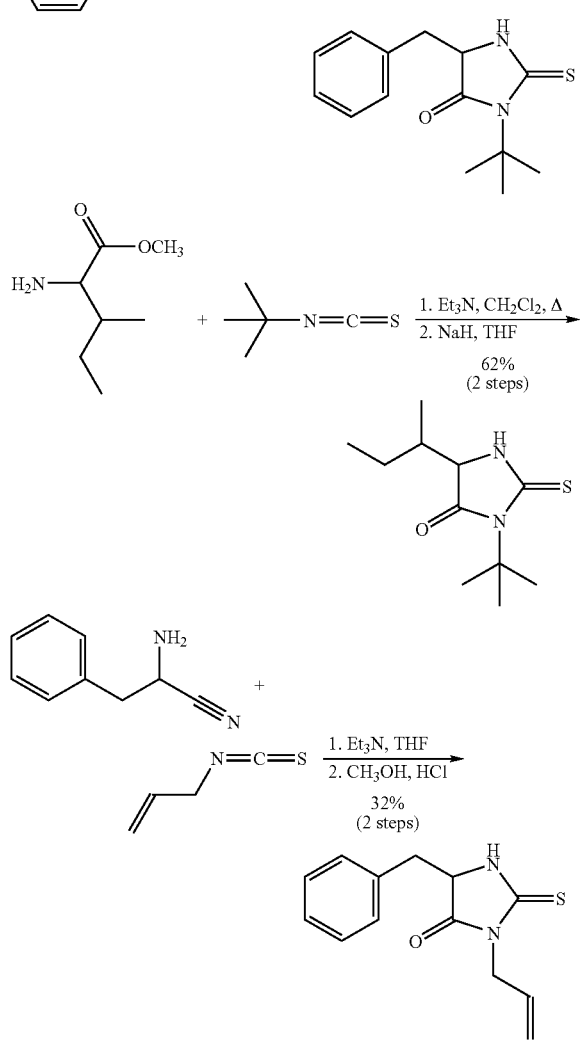

Reaction B: Condensation of thiohydantoin and 3-substituted thiohydantoins with carbonyl compounds to form alkylidene and arylidene thiohydantoins;

Initially, it may be useful to protect both at the sulfur and the 3-nitrogen. It is possible, albeit with low yield, to do this in the case of the isopropylidene compound by heating an acetone solution of thiohydantoin along with the protecting agent and diazabicycloundecene.

R'-allyl, 4-MeOBz, TBDMS

The S-protected thiohydantoin compounds or derivatives are quite sensitive to hydrolysis liberating mercaptans. It has been determined that the sulfur does not have to be protected to achieve successful synthesis. Several methods may be used to form alkylidene and arylidene thiohydantoins.

The first method involves heating a solution of the thiohydantoin in the carbonyl compound in the presence of an appropriate secondary amine (morpholine). Dehydration of the intermediate alcohol occurred spontaneously.

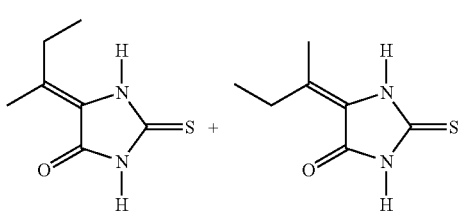

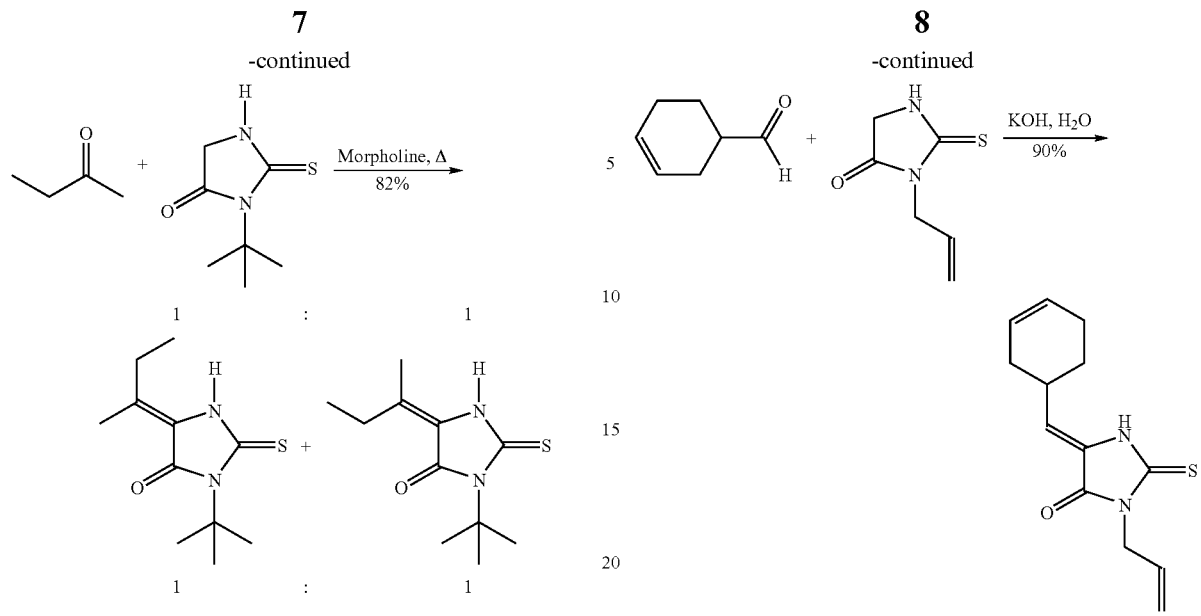

It is also possible to use a small amount of the carbonyl compound in solution with base. This reaction works very well if the solvent is water and the base is potassium hydroxide (the carbonyl compound need not be soluble).

Another successful method of practicing the present invention involves using aqueous triethylamine to form the intermediate alcohol. This could, with or without isolation, be dehydrated to the desired product by heating in aqueous acid.

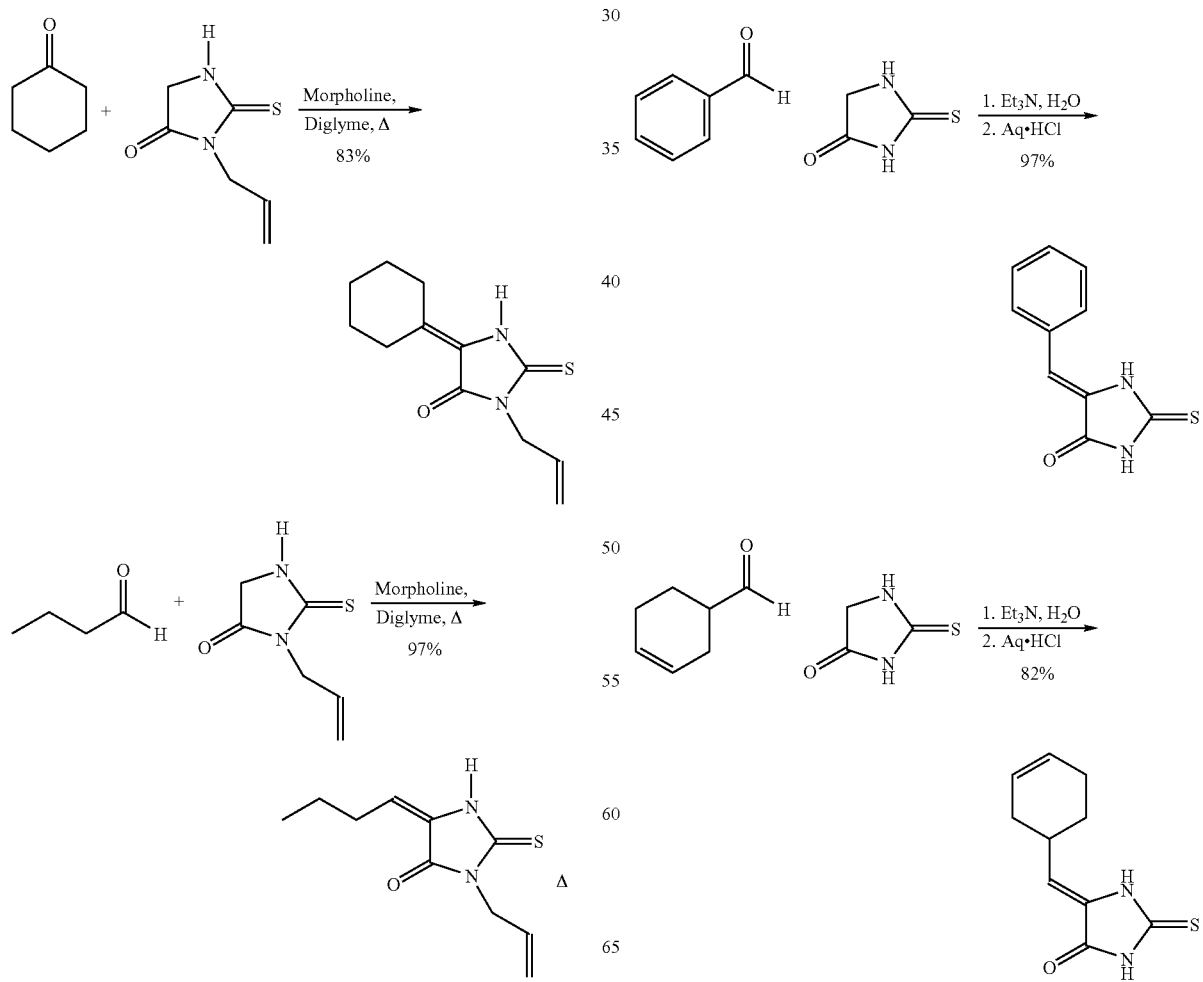

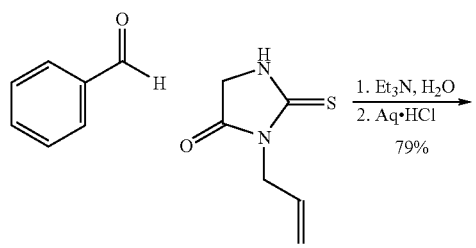

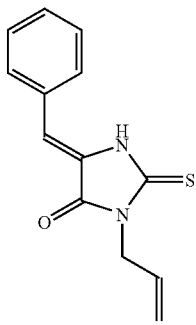

In the case of condensation with acetaldehyde, it is necessary to dehydrate the intermediate alcohol with strong base. Acid-catalyzed dehydration does not occur

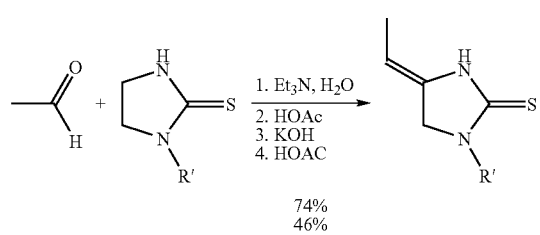

R' = allyl
R' = t-Bu

Interestingly, acetophenone does not react with 3-allyl-2-thiohydantoin under any of the above conditions. On the other hand, if the thiohydantoin dianion is generated with a strong base (in this case, lithium diisopropylamide [LDA] in THF), it is possible to form the arylidene 3-allyl-2-thiohydantoin. Similarly, in a more reluctant reaction, the arylidene 3-t-butyl-2-thiohydantoin is formed.

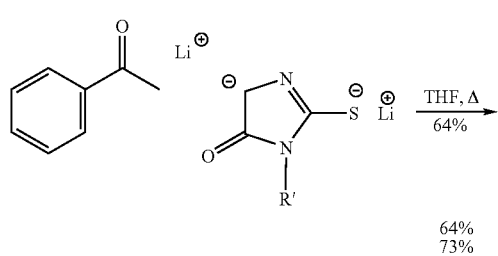

64%
73%

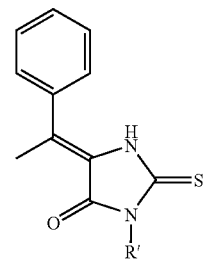

R' = allyl
  = t-butyl

Reaction C, 1,4-addition of hydride to arylidene and alkylidene thiohydantoins

Below are the results of various reduction attempts. Lithium aluminum hydride leaves a very large number of products. A number of substituted borohydrides reacted too slowly to be of use. Sodium borohydride, in one case, provides a smooth route to a 5-alkylthiohydantoin. It is of note that hydrogenation with a homogeneous catalyst is ineffective for this transformation.

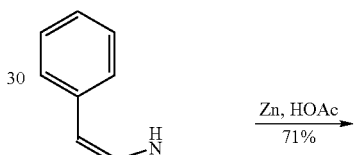

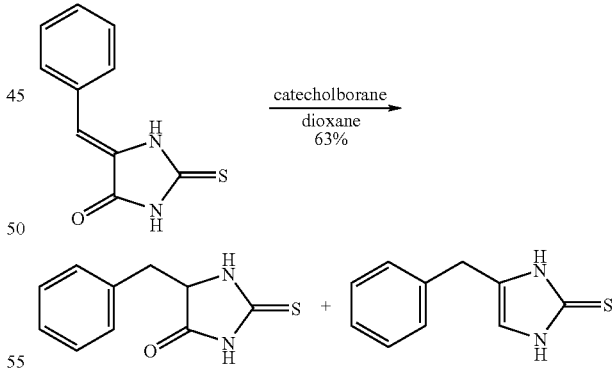

4 : 1

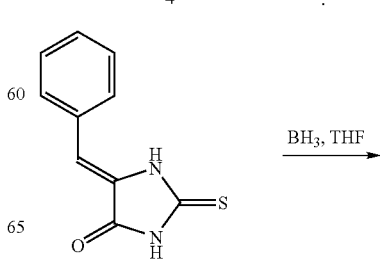

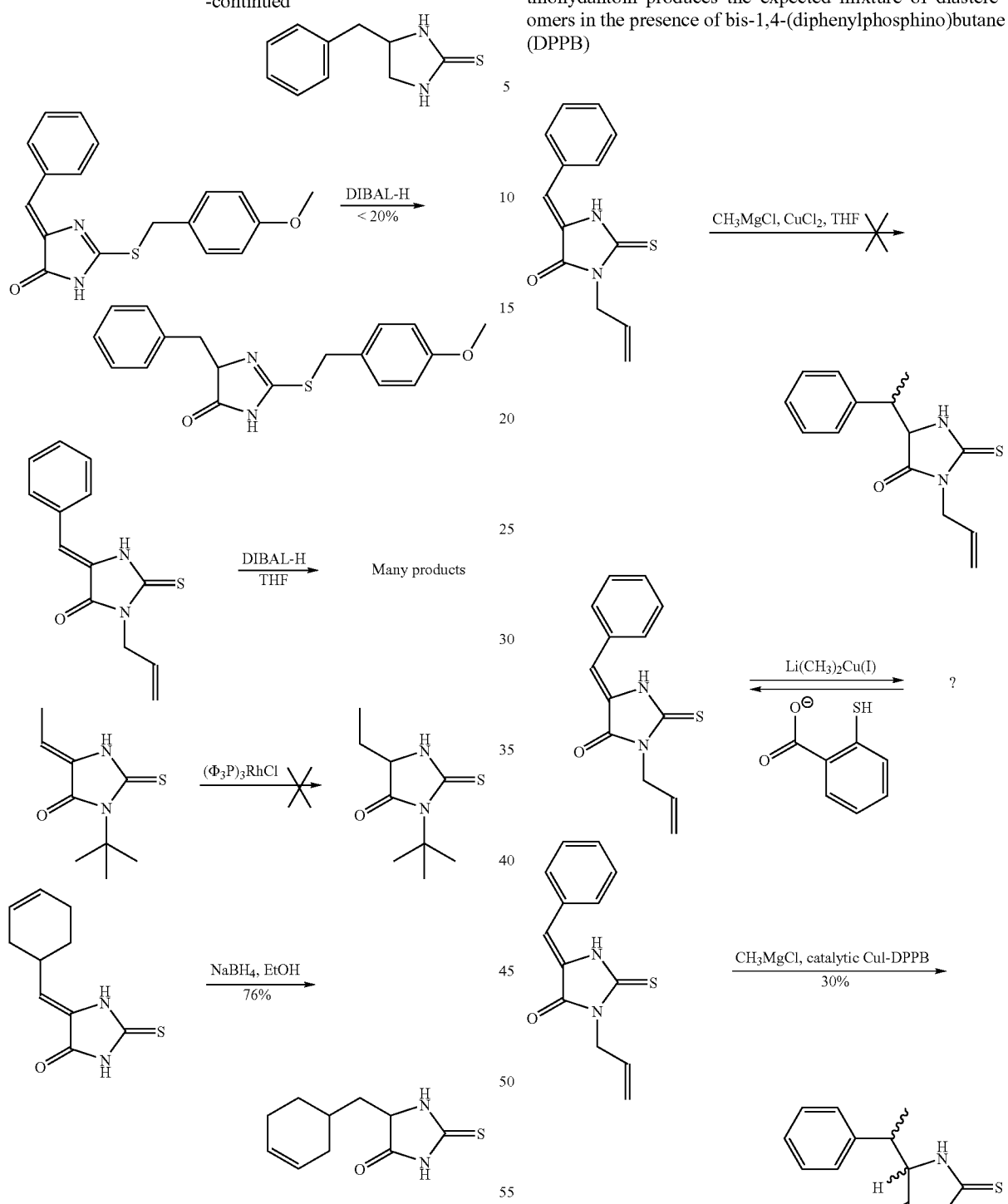

Reaction D. 1,4 Addition of metal alkyls to arylidene and alkylidene thiohydantoins The presence of the 2-thione causes problems with catalytic copper-mediated additions. Indeed, when stoichiometric copper, in the form of lithium dimethylcuprate, is used, there is formed a substance that reverted back to the starting material when treated with thiosalicylate.

This suggests that the catalytic reaction might occur if a chelating ligand is included in the reaction mixture. Indeed, copper-mediated Grignard addition to 3-allyl-5-benzylidene-thiohydantoin produces the expected mixture of diastereomers in the presence of bis-1,4-(diphenylphosphino)butane (DPPB)

One productive reaction of an S,N-diprotected thiohydantoin is the copper mediated 1,4-addition. In this case, an added ligand is not necessary. This suggests that the thiocarbonyl group, but not a thioether, binds sufficiently well with cuprous ion to prevent catalysis of the addition reaction.

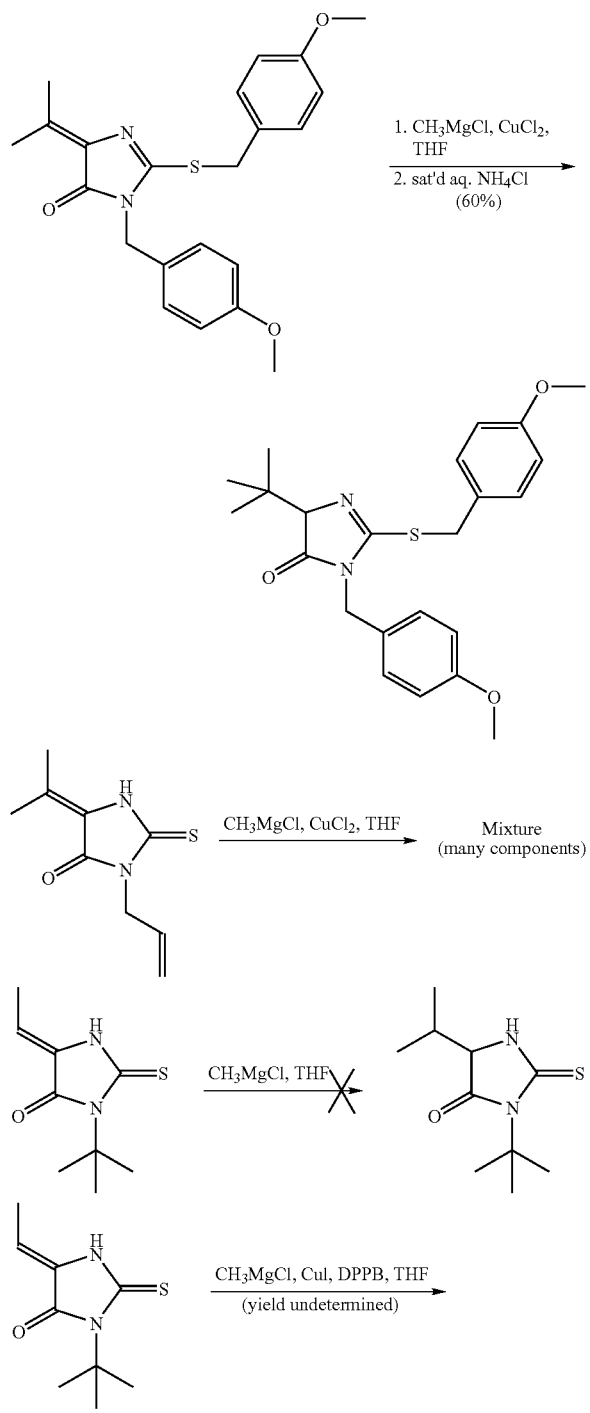

More interestingly, we found in a preliminary experiment that the low-temperature 1,4-addition of methyllithium to 3-t-butyl-5-ethylidene-2-thiohydantoin proceeds smoothly in the presence of stoichiometric amounts of sparteine, a chiral diamine that coordinates with metal alkyls.

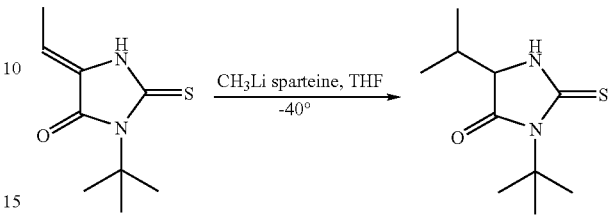

The low temperature 1,4-addition of diethylzinc proceeds at about the same rate with and without the presence of several copper-phosphorus catalysts. In no case is the desired product the major component of the reaction mixture.

Reaction E. Reduction of 5-substituted-thiohydantoins

The scheme below seems to account for results of reduction attempts. Under optimal conditions, formation of the overreduced substances III and IV are minimized, and accumulation of the productive intermediates A is maximized.

Of note is the observation that the product appears in the reaction mixture

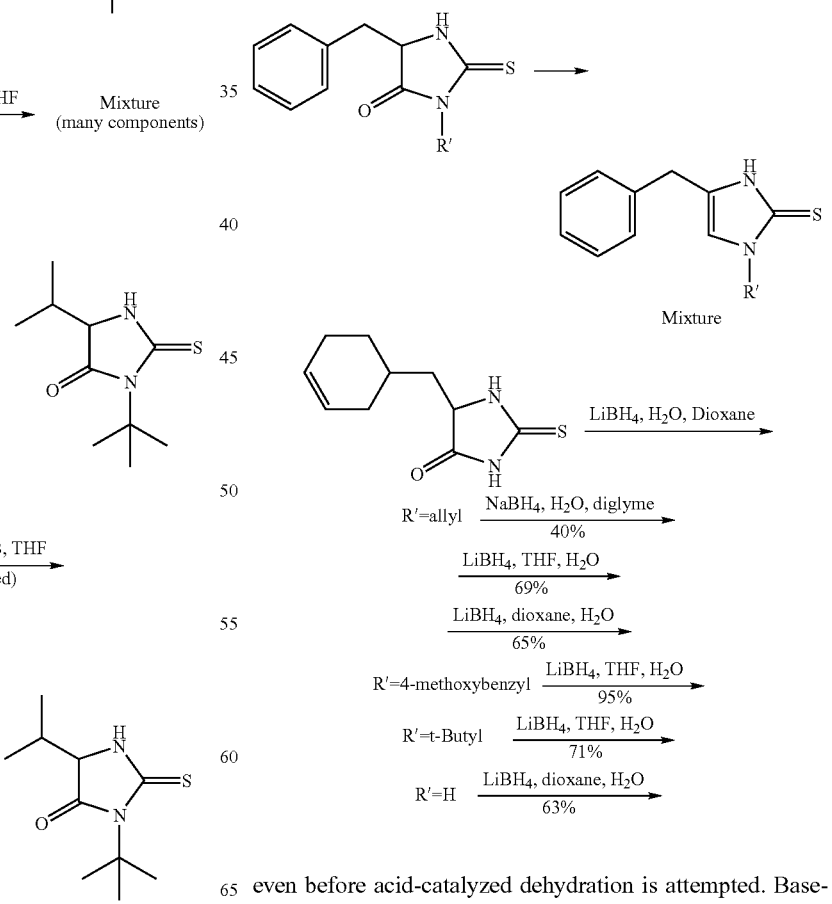

even before acid-catalyzed dehydration is attempted. Base-catalyzed elimination of an intermediate borate ester would account for this.

Reaction F. 1,4-+1,2-hydride additions in 1 step followed by dehydration.

It was also possible to produce 2-thioimidazoles directly from arylidene and alkylidene 2-thiohydantoins. In the case of N-protected compounds, conditions similar to those used for reduction of alkyl 2-thiohydantoins were sufficient. For unprotected compounds, best results were obtained in the presence of a hydrated salt ($CeCl_3$).

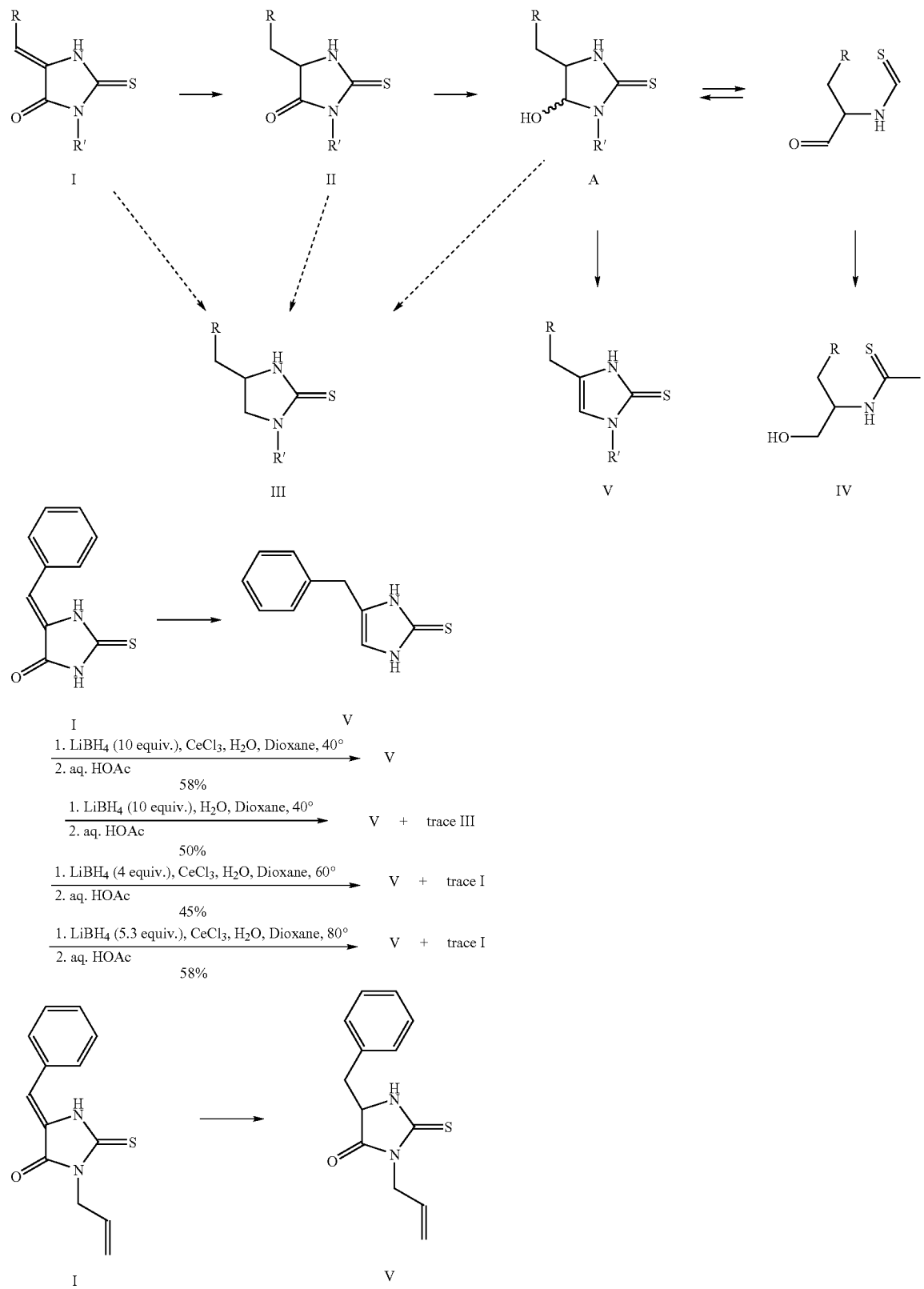

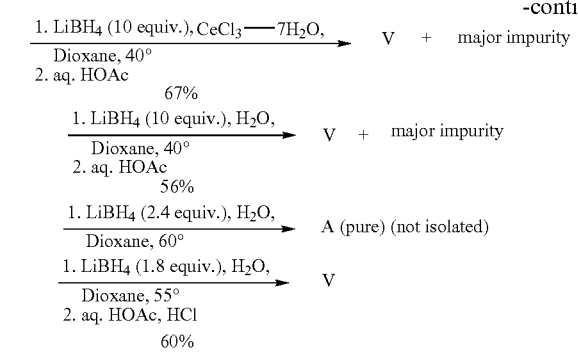

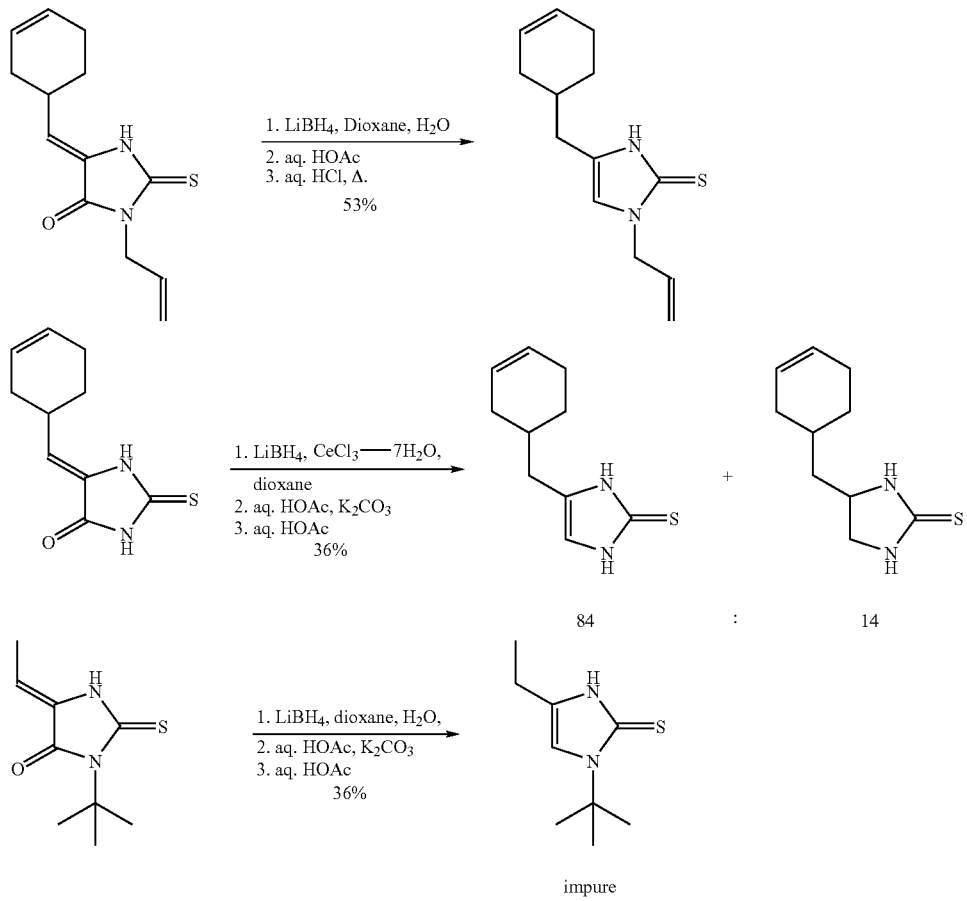

In the above reaction schemes, the symbols R, $R_1$, $R_2$, $R_3$ and $R^1$ are used to denote hydrogen, hydrocarbyl and substituted hydrocarbyl wherein said hydrocarbyl or substituted hydrocarbyl may be alkyl, alkenyl, alkynyl, aryl (including carbocyclic aryl and heterocyclic aryl) and alkaryl.

The following defined terms are used throughout this specification:

"Me" refers to methyl.

"Et" refers to ethyl.

"tBu" refers to t-butyl.

"iPr" refers to i-propyl.

"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond.

Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, NO₂, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, NO₂, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, NO₂, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)₂—R'''', where R'''' is aryl, C(CN)=C-aryl, CH₂CN, alkyaryl, sulfonamide, NH-alkyl, NH-alkylaryl, or NH-aryl.

R¹ and R² may form a condensed ring with C=O, e.g. as in cyclohexanone or cyclohenenone.

Preferably R is H, benzyl or CH₃CH₂CH(CH₃).
Preferably R₁ is H, CH₃, C₂H₅, phenyl or cyclohexenyl.
R' may be H, CH₂CHCH₂, (CH₃)₃C or p-methoxybenzyl.
Preferably R₂ is H or CH₃.
Preferably R₃ is H or alkyl.
M is a metal.
Ø is phenyl.
Bz is benzyl.
Preferably Y is OH, OCH₃ or CN.
Et is ethyl.
t-Bu is tertiary butyl.
DBU is diazabicycloundecane.

TBDMS is tertiarylbutyldimethysilyl.
DIBAL-H or DIBAL is diisobutyl aluminum hydride.
THF is tetrahydrofuran.
DPPB is bis-1,4-(diphenylphosphino) butane.
TFA is trifluoroacetic acid.
MsOH is methane sulfonic acid.

The invention is further illustrated by the following examples which are illustrative of a specific mode of practicing the invention and are not intended as limiting the scope of the claims.

EXAMPLES

General

NMR (nuclear magnetic resonance) spectra were taken either at 60 MHz on a Varian T-60 spectrometer or at 300 MHz on a Varian Inova system. The spectra of all intermediates were consistent with their structures. HPLC analyses of intermediates were performed using an Alltech Alltima column (C18, 5μ, 250×4.6 mm), with flow rate at 1.0 mL/min. Elution was isocratic using mixtures of water, A1 (700 mL of water, 300 mL of methanol, and 3 mL of triethylamine adjusted to pH 3.4 with phosphoric acid), and methanol. In general, the ratio of these components was 15:10:75. Other mixtures are noted. A diode array detector allowed us to monitor absorbance at numerous wavelengths associated with starting materials, intermediates, products, and impurities.

Example 1

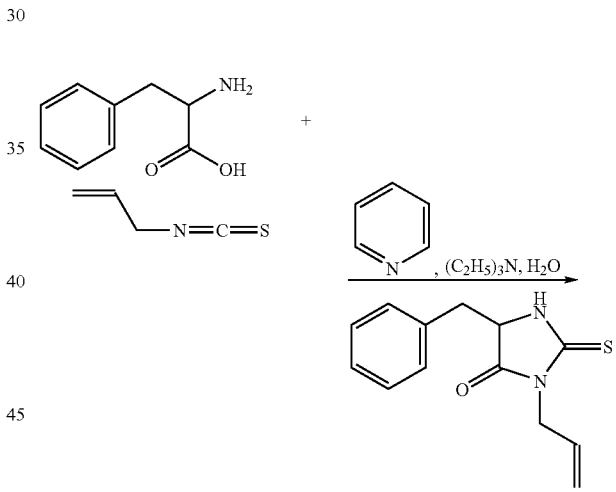

3-Allyl-5-benzyl-2-thiohydantoin

A flask equipped with a magnetic stirrer was charged with phenylalanine (15.8 g, 0.100 mol), triethylamine (11.1 g, 0.11 mol) pyridine (100 mL), and water (50 mL). Allyl isothiocyanate (10.4 g, 0.11 mol) was added to the flask, and the mixture was kept at 40-450 for 4 hr. the mixture was cooled to room temperature and was then extracted with 3×200 mL of toluene. The aqueous phase was mixed with concentrated hydrochloric acid (16 mL, 0.19 mol) and boiled gently for 45 min. The reaction mixture was stirred rapidly as it cooled to room temperature. It was further cooled in an ice-water bath for 20 min, and the solid that had formed was collected and washed with water.

The solid was dissolved in 80 mL of refluxing methanol. The volume was reduced to 70 mL on a hot plate. When the solution had cooled slightly, it was seeded with a very small portion of pure product. A solid mass rapidly formed in the flask. After 14 hours, the solid was collected, pressed well with rubber dam, and rinsed with 2×20 mL of methanol. The filtrate was left in a freezer for 30 min, and the resulting solid was collected and rinsed with several portions of freezer-cold methanol. The combined crops weighed 11.8 g (67%). NMR (CDCl$_3$, CD$_3$OD) δ 7.1 (s, 5H), 5.0-5.9 (m, 3H), 4.6 (s, [H2O, exchangeable proton]), 4.3 (d, 2H), 3.1 (d, 2H). An additional 3.8 g could be recovered from the toluene washes.

Example 2

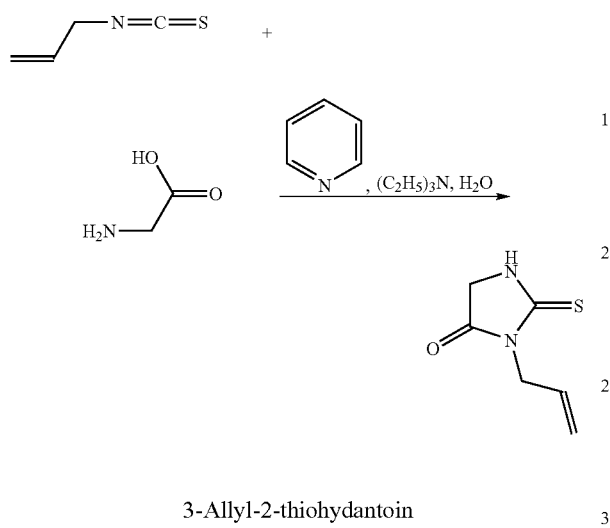

3-Allyl-2-thiohydantoin

Glycine (30 g, 0.40 mol), triethylamine (44 g, 0.44 mol), pyridine (100 mL), and water (100 mL) were mixed in a flask equipped with a magnetic stirrer and a temperature controller. Allyl isothiocyanate (44 g, 0.44 mol) was added, and the temperature was raised to 55° C. (the mixture became homogeneous at ca. 30°). When the mixture reached this temperature, it was allowed to cool to room temperature. The mixture was extracted with 3×200 mL of toluene to remove the pyridine and excess isothiocyanate and was then treated with 66 mL (0.8 mol) of concentrated hydrochloric acid. The mixture was heated at 90° C. for 2.5 hr and was then stirred rapidly while it cooled to room temperature. A solid mass of crystals formed instantaneously when the solution was seeded with a fragment of a crystal of authentic product. After the suspension stood at room temperature overnight, the product was collected and pressed with rubber dam. The filter cake was washed with 3×60 mL of water (the filter cake was pressed with rubber dam after each wash). After the material had dried to constant weight in a hood draft, it weighed 49 g (71% yield). NMR (CD$_3$OD) δ 4.9-6.1 (m, 3H), 4.6 (s, 1H), 4.3 (d, 2H), 4.0 (s, 2H). HPLC analysis showed no other components at several wavelengths.

Example 3

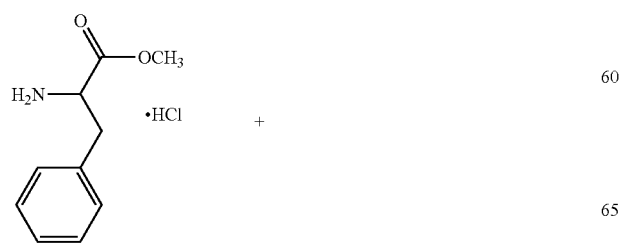

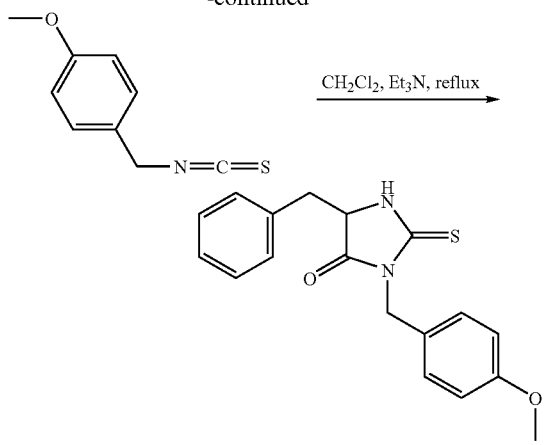

5-Benzyl-3-(4-methoxybenzyl)-2-thiohydantoin

L-Phenylalanine methyl ester hydrochloride (4.95 g, 0.023 mol) was suspended over dichloromethane (100 mL). Triethylamine (2.5 g, 0.025 mol) was added, and the mixture was stirred with a mechanical stirrer for 30 min. To the turbid mixture was added 4-methoybenzylisothiocyanate (4.47 g, 0.025 mol) in one portion. The resulting mixture was refluxed for 10 hr. The reaction mixture was diluted with dichloromethane (100 mL), washed with water (2×50 mL), brine (1×50 mL), filtered through 1 PS filter paper and concentrated under reduced pressure to give a viscous oil. The oil was mixed with 10% ethyl acetate/hexane (50 mL), and stirred for 60 min. The resulting solid was collected, washed with 10% ethyl acetate/hexane (25 mL), and air dried to give 7.4 g (98%) of 4-Benzyl-3-(4-methoxybenzyl)-2-thiohydantoin as a tan solid. HPLC analysis showed a purity of 97%. NMR (warm CDCl$_3$) δ 8.4 (s br, 1H), 6.9-7.6 (m, 9H), 5.0 (s, 2H), 4.2-4.6 (m, 1H), 3.9 (s, 3H), 2.8-3.4 (m, 2H).

Example 4

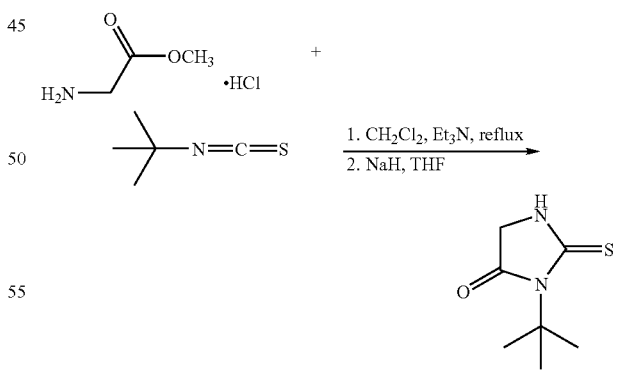

Methyl 2-(3-tert-butyl-1-thioureido)acetate

In a 2 L 3-necked flask equipped with a mechanical stirrer and a condenser was suspended glycine methyl ester hydrochloride (57.7 g, 0.46 mol) over dichloromethane (800 mL). Triethylamine (116.2 g, 1.15 mol) was added followed by addition of tert-butylisothiocyanate (46 g, 0.4 mol). The resulting mixture was refluxed for 3 hr and stirred at room temperature over night. The reaction mixture was washed with water (2×150 mL), 1M HCl (2×150 mL), sat. NaHCO3 (1×150 mL), brine (1×150 mL), filtered through 1 PS filter paper and concentrated under reduced pressure to give 78 g (95%) of methyl 2-(3-tert-butyl-1-thioureido)acetate as a white solid. HPLC analysis showed a purity of 95%. NMR (CDCl$_3$) δ 6.9 (s br, 2H), 4.6 (d, 2H), 3.9 (s, 3H), 1.6 (s, 9H).

3-tert-Butyl-2-thiohydantoin

Sodium hydride (9.9 g, 0.41 mol) was suspended over tetrahydrofuran (200 mL) under argon. The flask was cooled in a room temperature water bath and a solution of methyl 2-(3-tert-butyl-1-thioureido)acetate (76.5 g, 0.375 mol) in tetrahydrofuran (300 mL) was added over 75 min. After stirring for 30 min, the reaction mixture was diluted with ethyl acetate (500 mL), washed with 3M HCl (2×150 mL), brine (1×150 mL), filtered through 1 PS filter paper and concentrated under reduced pressure to give 63 g (98%) of 3-tert-Butyl-2-thiohydantoin as yellow solid. HPLC analysis showed a purity of 99%. NMR (CDCl$_3$) δ 8.3 (s br, 1H), 4.1 (s, 2H), 1.8 (s, 9H).

Example 5

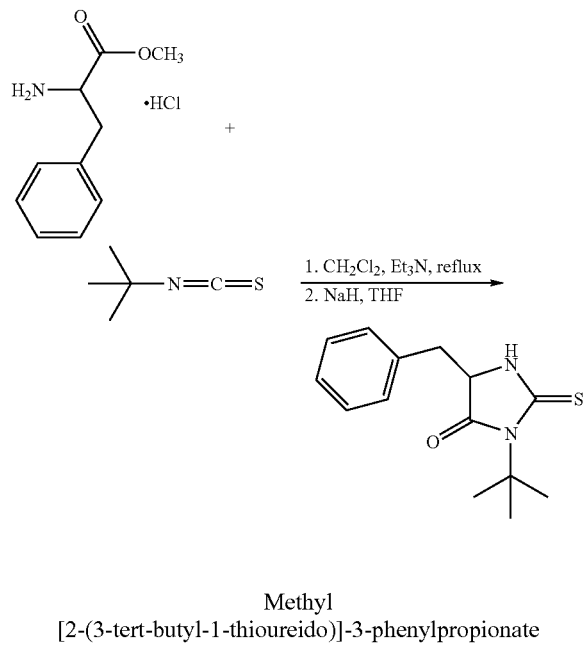

Methyl [2-(3-tert-butyl-1-thioureido)]-3-phenylpropionate

L-Phenylalanine methyl ester hydrochloride (2.16 g, 0.01 mol) was suspended over tetrahydrofuran (25 mL). Triethylamine (4.1 g, 0.04 mol) was added and stirred for 5 min. To this suspension was added tert-butylisothiocyanate (1.44 g, 0.0125 mol) in one portion. The resulting mixture was refluxed for 1 hr. The reaction mixture was diluted with water (25 mL), and extracted with ethyl acetate (1×35 mL). The organic layer was washed with brine (1×25 mL), filtered through 1 PS filter paper and concentrated under reduced pressure to give 2.9 g (100%) of product as an oil. HPLC analysis showed a purity of 97%. NMR (CDCl$_3$) δ 7.1-7.6 (m, 5H), 6.2-6.5 (m, 2H), 5.4-5.7 (m, 1H), 3.9 (s, 3H), 3.3-3.6 (m, 2H), 1.4 (s, 9H).

5-Benzyl-3-(tert-butyl)-2-thiohydantoin

Sodium hydride (0.26 g, 0.011 mol) was suspended over tetrahydrofuran (10 mL) under argon. A solution of 1-tert-butyl-3-(methyl 3-phenyl propionate)-2-thiourea (2.94 g, 0.01 mol) in tetrahydrofuran (5 mL) was added over 15 min. After stirring for 15 min, HPLC analysis showed the reaction was complete. The reaction mixture was diluted with ethyl acetate (40 mL), washed with water (2×15 mL), brine (1×15 mL), filtered through 1 PS filter paper and concentrated under reduced pressure to give 2.8 g (85%) of 5-Benzyl-3-(tert-butyl)-2-thiohydantoin as an oil. HPLC analysis showed a purity of 88%. NMR (CDCl$_3$) δ 8.3 (s br, 1H), 7.5 (s, 5H), 4.2-4.4 (m, 1H), 3.1-3.4 (m, 2H), 1.7 (s, 9H).

Example 6

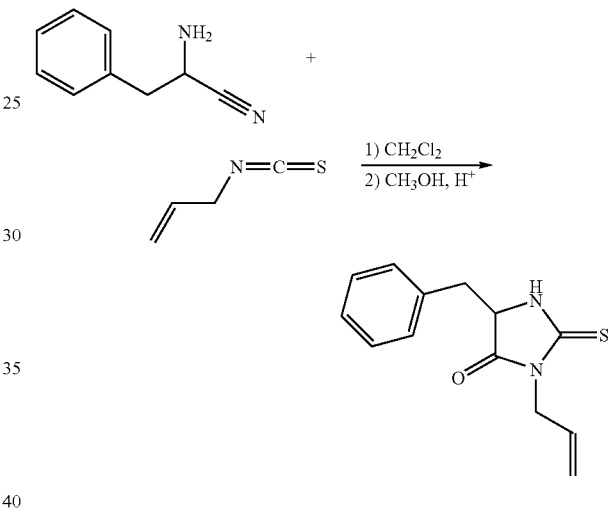

2-(3-Allyl-1-thioureido)-3-phenylpropionitrile

To a solution of 2-amino-3-phenylpropionitrile (5.84 g, 0.04 mol) in tetrahydrofuran (25 mL) was added allylisothiocyanate (4.75 g, 0.048 mol) under argon. The reaction mixture was stirred at room temperature for 1 hr and then concentrated under reduced pressure to give 10 g (100%) of product as an oil. HPLC analysis showed a purity of 90%. NMR (CDCl$_3$) δ 7.4 (s, 5H), 6.4-6.9 (m, 2H), 5.0-6.2 (m, 4H), 4.1 (t br, 2H), 3.2 (d, 2H).

5-Benzyl-3-allyl-2-thiohydantoin

To a solution of crude 1-Allyl-3-[2-(3-phenyl propionitrile)]-2-thiourea (7.35 g, 0.03 mol) in methanol (10 mL) was added concentrated hydrochloric acid (10 mL). The resulting mixture was heated at reflux on a steam bath for 1 hr. The reaction mixture was mixed with water (25 mL) and cooled in an ice-water bath. The light brown solid was collected and dissolved in a hot mixture of 30% water in ethanol (50 mL). After the mixture had cooled to room temperature, a white solid was collected and air dried to give 2.35 g (32%) of 5-benzyl-3-allyl-2-thiohydantoin. HPLC analysis showed a purity of 96%. NMR (CDCl$_3$) δ 8.3 (s br, 1H), 7.4 (s, 5H), 5.0-6.2 (m, 3H), 4.5 (t br, 3H), 3.0-3.4 (m, 2H).

Example 7

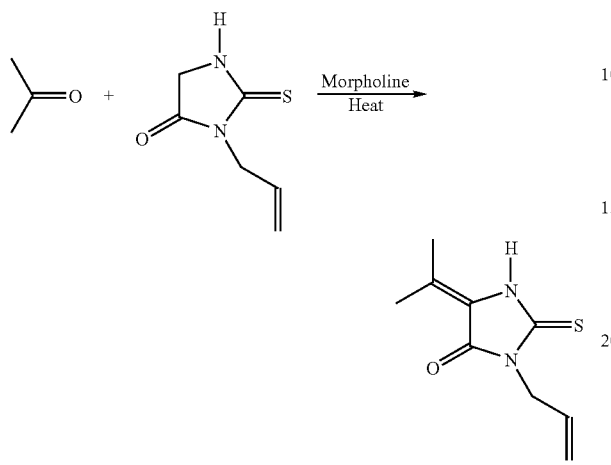

3-Allyl-5-isopropylidene-2-thiohydantoin

A flask equipped with a reflux condenser and nitrogen atmosphere was charged with acetone (20 mL), 3-allylthiohydantoin (2.0 g, 0.013 mol), and morpholine (1.1 g, 0.013 mol). The mixture was heated at reflux for 80 min and, after cooling, was diluted with 40 mL of ethyl acetate. The resulting solution was washed with 2×20 mL 1.2 M HCl, 20 mL of water, and 20 mL of saturated aqueous NaCl. The solution was then filtered through 1 PS paper and concentrated to dryness at aspirator pressure and then high vacuum. The off-white crystalline residue weighed 2.3 g (92%). No other components were detectable by HPLC at 215 nm. NMR (CDCl$_3$) δ 9.9 (bs, 1H), 5.1-6.1 (m, 3H), 4.6 (d, 2H), 2.3 (s, 3H), 2.0 (s, 3H).

Example 8

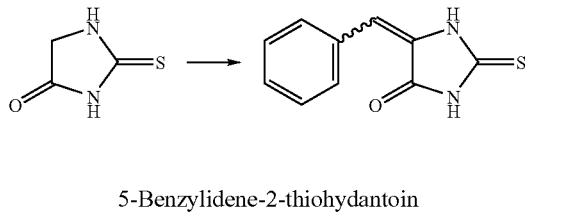

5-Benzylidene-2-thiohydantoin

A flask equipped with a magnetic stirrer, nitrogen pressure, and reflux condenser was charged with thiohydantoin (24.9 g, 0.215 mol), benzaldehyde (22.8 g, 0.215 mol), triethylamine (43 g, 0.43 mol), and water (250 mL). Slight warming and vigorous stirring brought everything into solution. The mixture was stirred overnight and then transferred to an Erlenmeyer flask equipped with a magnetic stirrer. The pH was brought to ca. 3 with 3 M hydrochloric acid, and the mixture was stirred for 3 hr. The resulting solid was collected and washed with water and 2×50 mL of diethyl ether. The product weighed 97.6 g (97%). No other components were found in an HPLC trace at 260 and 350 nm. NMR (d$_6$-DMSO) δ 7.2-7.8 (m, 5H), 6.4 (s, 1H), 3.5 (bs, 2H).

Example 9

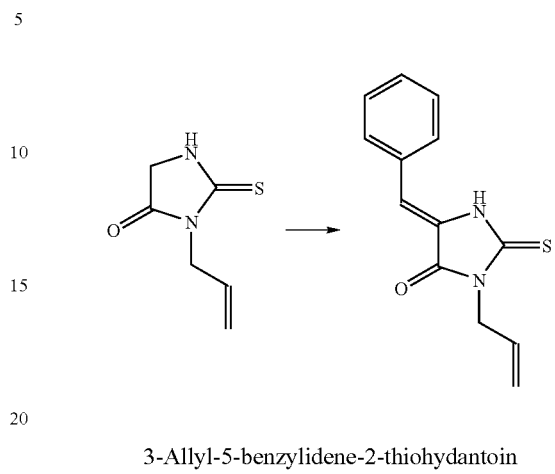

3-Allyl-5-benzylidene-2-thiohydantoin

A flask equipped with a magnetic stirrer, condenser, and nitrogen pressure was charged with 3-allylthiohydantoin (15 g, 0.096 mol), water (90 mL), and benzaldehyde (10.2 g, 0.096 mol). As the mixture was stirred, triethylamine (19.4 g, 0.192 mol) was added slowly. After 18 hr, HPLC analysis indicated the absence of starting material, and the mixture was transferred to an Erlenmeyer flask. The mixture was stirred vigorously as 3 M hydrochloric acid was added dropwise until the pH reached 3 (65 mL). The mixture was stirred for an additional 90 min, and then the solid that had formed was collected by filtration. The still wet solid was resuspended in 100 mL of water, stirred for 30 min, and collected. After air drying, the orange solid weighed 18.4 g (79%). HPLC analysis indicated a purity of 95% at 215 nm. NMR (CDCl$_3$) δ 9.3 (bs, 1H), 7.4 (s, 5H), 6.8 (s, 1H), 5.1-6.3 (m, 3H), 4.6 (d, 2H).

Example 10

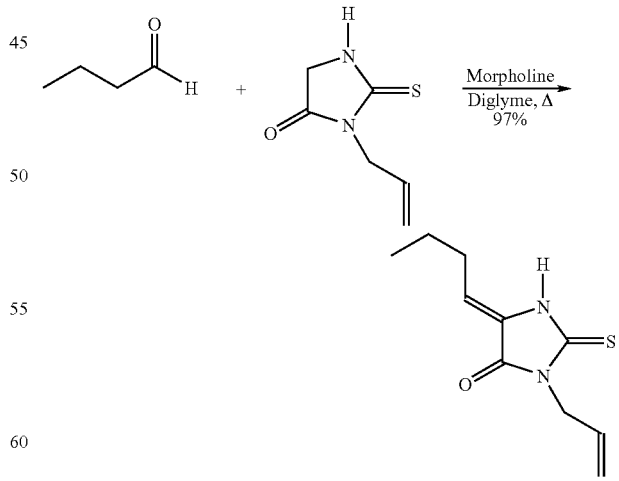

3-Allyl-5-n-butylidene-2-thiohydantoin

A flask equipped with a reflux condenser, magnetic stirrer, and nitrogen atmosphere was charged with diglyme (10 mL), 3-allylthiohydantoin (1.0 g, 0.0064 mol), morpholine (0.56 g, 0.0064 mol), and freshly distilled butyraldehyde (0.94 g, 0.13 mol). The mixture was heated in a 70° oil bath for 250 min and, after cooling, was diluted with 20 mL of ethyl acetate. The resulting solution was washed with 2×10 mL 1.2 M HCl, 10 mL of water, and 10 mL of saturated aqueous NaCl. The solution was then filtered through 1 PS paper and concentrated to dryness at aspirator pressure and then high vacuum. The light orange crystalline residue weighed 1.26 g (97%). An HPLC trace at 215 nm indicated that the major product comprised 92% of the mixture. Another component (5%), with a nearly identical ultraviolet spectrum, eluted slightly more slowly. This possibly represents the other geometric isomer. NMR (CDCl$_3$) δ 10 (bs, 1H), 5.2-6.3 (m, 4H), 4.6 (d, 2H), 2.3 (quart., 2H), 1.8 (sex., 2H), 1.0 (t, 3H).

Example 11

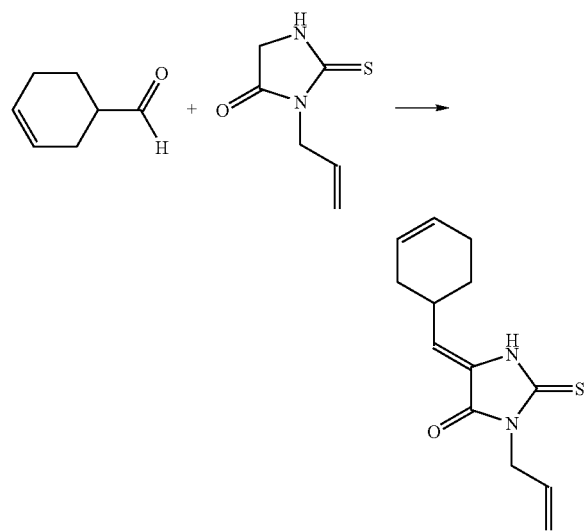

3-Allyl-5-(1,2,3,6-tetrahydrobenzylidene)-2-thiohydantoin

To a solution of potassium hydroxide (14.3 g, 0.256 mol) in water (400 mL) was added 3-allyl-2-thiohydantoin (20 g, 0.128) followed by 1,2,3,6-tetrahydrobenzaldehyde (15.5 g, 0.14 mol). The reaction mixture was stirred at room temperature for 15 min. At this time HPLC analysis indicated completion of the reaction. The reaction mixture was acidified with 3M HCl.

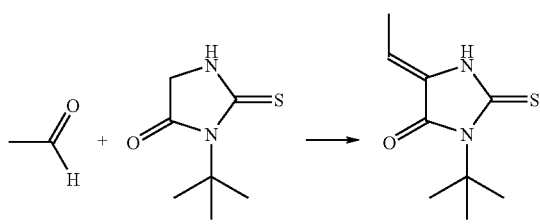

After stirring for 30 min, yellow solid was collected, washed well with water and air dried to give 28.45 g (90%) of 3-Allyl-5-(1,2,3,6-tetrahydrobenzylidene)-2-thiohydantoin.

HPLC analysis at 325 nm showed a purity of 100% (two isomers in ratio of 95:5). NMR (CDCl$_3$) δ 10.3 (s br, 1H), 5.2-6.3 (m, 6H), 4.6 (d, 2H), 1.4-3.1 (m, 7H).

Example 12

3-tert-Butyl-5-ethylidene-2-thiohydantoin

To a solution of 3-allyl-2-thiohydantoin (12.04 g, 0.07 mol) in glyme (75 mL) was added water (75 mL) followed by addition triethylamine (14.14 g, 0.14 mol). The resulting mixture was cooled to 5° C., and then acetaldehyde added all in one portion. The internal temperature went up to 10° C. The cooling bath was removed and the resulting mixture was stirred at room temperature for 2 hr. To the reaction mixture was added ethyl acetate (150 mL) and acidified with acetic acid (8.4 g, 0.14 mol). Aqueous layer was separated and extracted with ethyl acetate (50 mL). The combined organic layers were washed with brine (1×100 mL), filtered through 1 PS filter paper and concentrated under reduced pressure to give 20 g of two isomeric alcohols (intermediate) as a red oil. NMR (CDCl$_3$) δ 8.4 (s br, 1H), 5.0 (s br, 2H), 4.1-4.7 (m, 2H), 1.8 (s, 9H), 1.0-1.5 (m, 3H).

A solution of potassium hydroxide (6.45 g, 0.115 mol) in water (150 mL) was added to the crude alcohols (20 g). The resulting mixture was stirred vigorously for 2.5 hr, and then filtered through #54 filter paper. The filtrate was acidified with acetic acid (7.23 g, 0.12 mol) and extracted with dichloromethane (2×200 mL). The combined organic layers were washed with brine (1×100 mL), filtered through 1 PS filter paper and concentrated under reduced pressure to give 12.5 g of a viscous oil. The oil was flash chromatographed on a 200 g flash chromatography silica gel with 20 g of anhydrous sodium sulfate on top. The column was eluted with 200 mL portions of 50% dichloromethane in hexane for fractions 1-7, and dichloromethane for fractions 8-14. The product eluted in fractions 8-13 (TLC solvent: ethyl acetate/hexane; 1:2) to give 6.3 g (46%) of 3-tert-Butyl-5-ethylidene-2-thiohydantoin as yellow solid. HPLC analysis showed a mixture of two isomers in ratio of 96 to 4. NMR (CDCl$_3$) δ 10.4 (s br, 1H), 6.2 (q, 1H), 2.1 (s, 3H), 2.0 (s, 9H).

Example 13

3-Allyl-5-(α-methylbenzylidene)-2-thiohydantoin

A solution of 3-allyl-2-thiohydantoin (1.56 g, 0.010 mol) and acetophenone (1.56 g, 0.013 mol) in THF (50 mL), maintained under an argon atmosphere, was treated with a 1.5 M cyclohexane solution (15 mL, 0.026 mol) of lithium diisopropylamide-THF. After the addition, the reaction temperature rose from room temperature to 40° C. The mixture was stirred overnight. It was then diluted with ethyl acetate (50 mL), washed with 1 M HCl (2×85 mL), and brine (85 mL), filtered through 1 PS paper, and concentrated under reduced pressure to give 3.1 g of a viscous brown oil. The oil was separated chromatographically on 50 g of flash silica gel in a column topped with 10 g of anhydrous Na$_2$SO$_4$. The column was eluted with 50 mL portions of 30% dichloromethane in hexanes for fractions 1-4, 65% dichloromethane in hexanes for fractions 5-8, and dichloromethane for fractions 9-12. The product was eluted in fractions 7-11 (as detected by TLC with EtOAc as eluent) to give an oil that was contaminated with acetophenone. The oil was triturated with hexanes. The suspension was cooled in a freezer for 30 min, and then the solid was collected, washed with 10 mL of cold hexanes, and air dried to give 1.65 g (64%) of the title compound. HPLC analysis showed a purity of 97%. NMR (CDCl$_3$) δ 8.7 (bs, 1H), 7.7 (s, 5AH), 5.1-6.5 (m, 3H), 4.6 (d, 2H), 2.7 (s, 3H).

Example 14

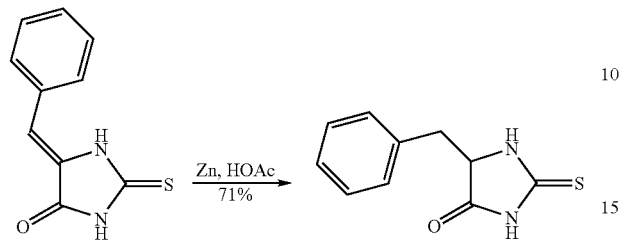

5-Benzyl-2-thiohydantoin

5-Benzylidene-2-thiohydantoin (24.5 g, 0.12 mol) was dissolved in 150 mL of acetic acid in a flask equipped with a thermometer, a mechanical stirrer, a reflux condenser, and argon pressure. Zinc dust (11.8 g, 0.18 mol) was added, and the flask was immersed in a 130° bath. After 2.5 hr at reflux, HPLC analysis showed no starting material. The mixture was allowed to cool to 50°, and a 500 mL portion of methanol was added. The mixture was returned to reflux, for about 5 min and was then allowed to cool to 63°. The hot mixture was filtered through Whatman #4 paper. The filtrate was concentrated to a paste in vacuo. The residue was mixed with 400 mL of a 3:7 mixture of isopropanol:dichloromethane. The solution was filtered and washed with 1×200 mL and 1×100 mL of water and 1×100 mL of saturated aqueous sodium chloride. After the solution had been filtered through 1 PS paper, it was concentrated at aspirator pressure and high vacuum to yield 17.5 g (71%). HPLC analysis indicated a purity of 78% at 210 nm. NMR (d$_6$-DMSO) δ 12.1 (bs, 1H), 10.7 (bs, 1H), 7.8 (s, 5H), 5.2 (t, 1H), 3.6 (d, 2H).

Example 15

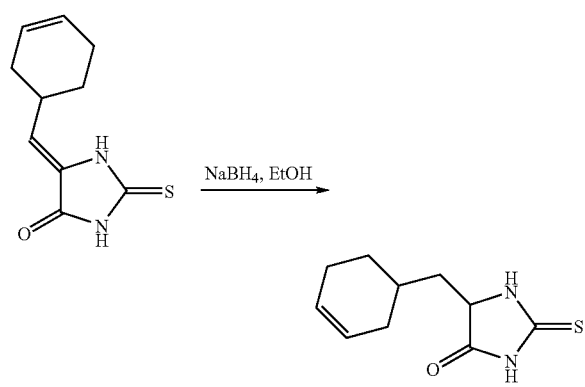

5-(1,2,3,6-tetrahydrobenzyl)-2-thiohydantoin

A solution of 5-(1,2,3,6-tetrahaydrobenzylidene)-2-thiohydantoin (0.21 g, 0.0010 mol) in 4 mL ethanol was mixed with NaBH$_4$ (0.076 g, 0.0020 mol) in 4 mL of ethanol. After 25 min, no further progress had occurred relative to after 5 min. An additional portion (0.020 g, 0.00053 mol) of sodium borohydride was added. After an additional 40 min, the mixture was adjusted to pH 4.5 with 10% aqueous acetic. It was then diluted with 10 mL of water and stirred for 2 hr. The resulting solid was collected and washed with 4×1 mL of water. After drying overnight in an hood draft, the product weighed 0.16 g (76%). An HPLC trace (30:25:45—H$_2$O:Al:CH$_3$OH) at 215 nm showed 93% @ 8.8 minutes. Another 5% @ 11.7 min was starting material. NMR (d$_6$-DMSO) δ 12 (bs, 1H), 10.5 (bs, 1H), 6.0 (s, 2h), 4.6 (m, 1H), 1.4-3.1 (m, 7H).

Example 16

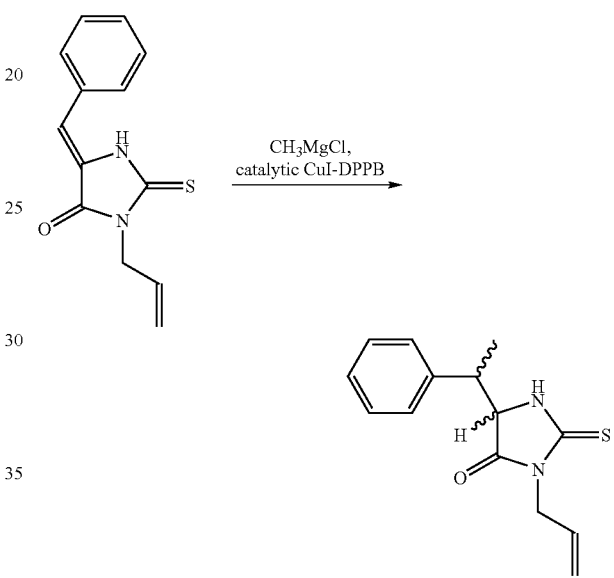

5-(α-Methylbenzyl)-2-thiohydantoin

CuI (0.019 g, 0.00010 mol) was suspended in 8 mL of THF in a flask equipped with a septum, a magnetic stirrer, and nitrogen pressure. To this was added 1,4-bis(diphenylphosphino)butane (DPPB) (0.085 g, 0.00020 mol). The mixture was stirred for 5 min, and then a 3 M methylmagnesium chloride (1.7 mL, 0.0050 mol) in THF was added by syringe. After 5 additional min, the flask was immersed in an ice-water bath. The 3-allyl-5-benzylidenethiohydantoin (0.49 g, 0.0020 mol) was added as a solid in 1 portion. After 45 min the reaction mixture was diluted with 10 mL of THF and 25 mL of saturated aqueous NH$_4$Cl. The layers were separated, and the organic layer was concentrated in vacuo. The residue was mixed with 5 mL of methanol. The resulting solid was filtered off under vacuum. The filter cake was washed w 2×1 mL of methanol, and the combined filtrates were concentrated at aspirator pressure and then high vacuum. The residue (0.51 g) was separated in 3 passes through Biotage 12 mm silica gel columns. A gradient of 0-10% EtOAc in hexanes with 9 mL fractions over 430 mL allowed recovery of 0.06 g of 1 of the diastereomers and 0.11 g of the other. The total amount recovered represented a 30% yield. Both HPLC traces and 60 MHz NMR spectra showed small amounts of the other isomer in each of these. NMR (1 isomer), (CDCl₃) δ 7.8 (bs, 1H), 7.3 (s, 5H), 4.8-6.1 (m, 3H), 4.4 (m, 3H), 3.5 (m, 1H), 1.4 (d, 3H).

Example 17

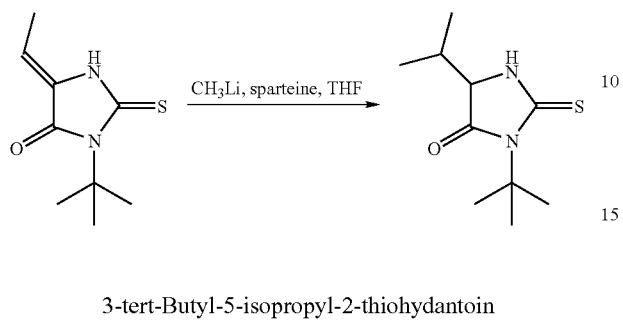

3-tert-Butyl-5-isopropyl-2-thiohydantoin

Sparteine (0.94 g, 0.0040 mol) was dissolved in 2 mL of THF in a flask equipped with a magnetic stirrer, septum, and nitrogen pressure. The flask was immersed in a −40° bath, and a 1.6 M ethereal solution of methyllithium (2.5 mL, 0.0040 mol) was added by syringe. Then a solution of 3-t-butyl-5-ethylidenethiohydantoin (0.20 g, 0.0010 mol) in 2 mL of THF was added dropwise by syringe over 20 min. After 1 hr, HPLC analysis showed no starting material. The reaction mixture was diluted with 5 mL of saturated aqueous NH₄Cl, then 4 mL of 1 M HCl, and then 10 mL of EtOAc. The layers were separated, and the organic layer was washed with 2×30 mL of 1 M HCl. The solvent was removed at aspirator pressure, and the residue was reconcentrated×3 from small amounts of dichloromethane. An HPLC trace at 270 nm revealed a purity of only 71% for the major product, although there was no major impurity. NMR (CDCl₃) δ 8.5 (bs, 1H), 3.8 (m, 1H), 0.9-2.8 (m, 16H). It is notable that the methyls of the isopropyl group are magnetically nonequivalent.

Example 18

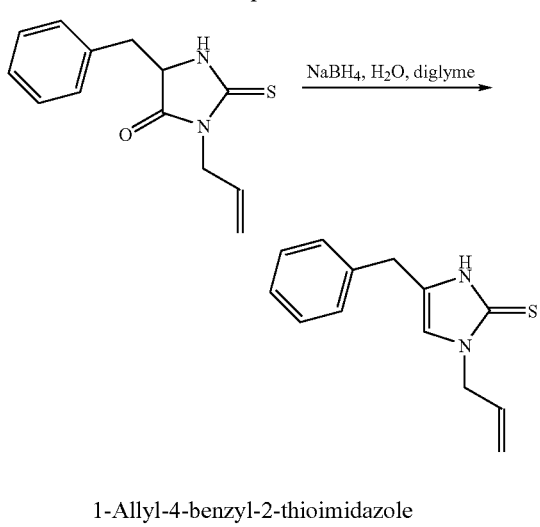

1-Allyl-4-benzyl-2-thioimidazole

A solution of 3-allyl-5-benzyl-2-thiohydantoin (4.90 g, 0.020 mol) in 45 mL of diglyme was stirred magnetically as a solution of sodium borohydride (2.0 g, 0.053 mol) in water (45 mL) was added. After ca. 18 hr, only a trace of starting material remained (as judged by HPLC). The reaction was quenched by the addition of 5 mL (ca. 0.06 mol) of concentrated hydrochloric acid. After about 10 min, the mixture became homogeneous. After the mixture had cooled, it was diluted with 150 mL of water, and the resulting oily suspension was stirred rapidly. After it had stirred overnight, the solid that had formed was collected and washed with several portions of water. After drying, the solid weighed 1.86 g (40%). HPLC analysis at 270 nm indicated a purity of 95%. The NMR spectrum was consistent with the structure. Notable was the ring proton at 6.7 ppm.

Example 19

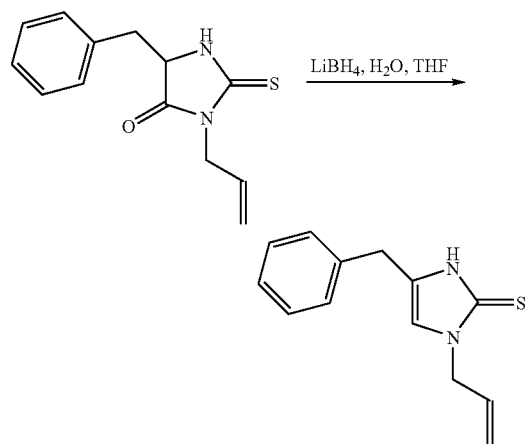

1-Allyl-4-benzyl-2-thioimidazole

3-Allyl-5-benzyl-2-thiohydantoin (0.62 g, 0.0025 mol) was dissolved in tetrahydrofuran (2.5 mL) under argon. A solution of lithium borohydride (1.25 mL of 2M LiBH₄ in THF, 0.0025 mol) was added. This was followed by the addition of 5 drops of water. After the reaction mixture had stirred 5 min at room temperature, 5 more drops of water were added, and resulting mixture was warmed to 50° C. After 20 min, HPLC indicated that the reaction was complete. The reaction mixture was cooled to room temperature and acidified with 3M HCl (5 mL). Water (15 mL) was added, and the mixture was stirred at room temperature overnight. A white solid was collected and air dried to give 0.4 g (69%) of 1-Allyl-4-benzyl-2-thioimidazole as a white solid. HPLC analysis showed a purity of 97%. NMR (CDCl₃: d₆-DMSO, warm) δ 12.5 (s br, 1H), 7.5 (s, 5H), 6.7 (s, 1H), 5.0-6.3 (m, 3H), 4.6 (d, 2H), 3.7 (s, 2H).

Example 20

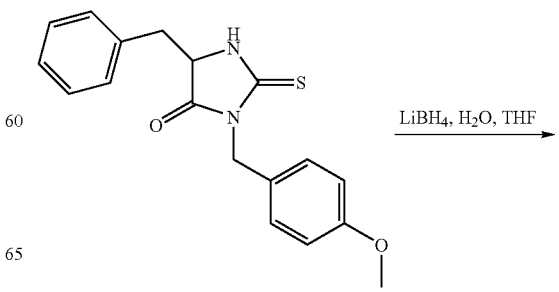

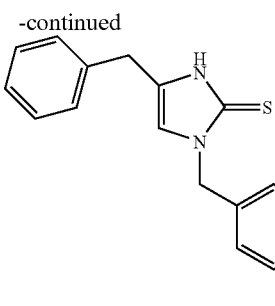

4-Benzyl-1-(4-methoxybenzyl)-2-thioimidazole

5-Benzyl-3-(4-methoxybenzyl)-2-thiohydantoin (5.87 g, 0.018 mol) was dissolved in tetrahydrofuran (25 mL) under argon. A solution of lithium borohydride (9 mL of 2M LiBH$_4$ in THF, 0.018 mol) was added, and the resulting mixture was warmed to 50° C. Water (0.5 mL) was added dropwise. After 15 min another 0.5 mL of water was added. After 15 additional min the last portion of water (0.5 mL) was added. After 10 min, HPLC indicated that the reaction was complete. The reaction mixture was cooled to room temperature and acidified with 3M HCl (25 mL). Water (100 mL) added, and the mixture was stirred at room temperature for 1 hr. The resulting white solid was collected and air dried to give 5.32 g (95%) of 4-benzyl-1-(4-methoxybenzyl)-2-thioimidazole. HPLC analysis showed a purity of 97%. NMR (CDCl$_3$) δ 12.4 (s br, 1H), 7.0-7.7 (m, 9H), 6.5 (s, 1H), 5.3 (s, 2H), 4.6 (d, 2H), 3.9 (two overlapped s, 5H).

Example 21

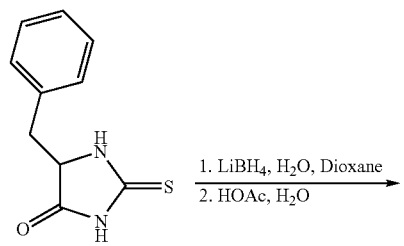

4-Benzyl-2-thioimidazole

A flask equipped with a large magnetic stir bar and nitrogen atmosphere was charged with dioxane (20 mL) and LiBH$_4$ (2.2 g, 0.10 mol). The borohydride was not completely in solution. The suspension was stirred rapidly as 0.90 g (0.050 mol) of water was slowly added. The flask was immersed in a 40° bath, and the mixture was stirred for 15 minutes. This resulted in formation of a white paste. The flask was removed from the bath and allowed to cool to room temperature. 5-Benzylthiohydantoin (2.06 g, 0.010 mol) in 20 mL of dioxane was added in 1 portion. After gas evolution had ceased, the flask was again immersed in a 40° bath. The mixture was stirred for 40 min, and then an additional 0.50 g (0.028 mol) of water was added. After an additional 50 min, the mixture was very slowly added to an ice-cold solution of 12 g (0.20 mol) of acetic acid in 110 mL of water. The mixture was boiled for ca. 10 min, and then K$_2$CO$_3$ was added until the pH was >10. A small amount of "tar" that formed on the surface was skimmed off, and the mixture was stirred overnight.

After 14 hr, the resulting solid was collected and washed with 2×10 ml of water. After drying, the product, 4-benzyl-2-thioimidazole, weighed 1.2 g (63%). HPLC analysis indicated a purity>98% at 215, 240, 262 (λ$_{max}$), and 270 nm. The over reduced imidazolidine-2-thione was not detected in the solid, although it did appear in the filtrate. The 60 MHz NMR spectrum contained only the expected peaks and a trace peak for water.

Example 22

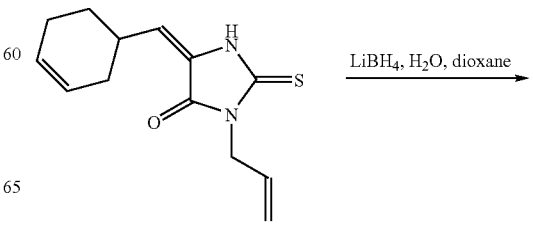

4-Benzyl-1-tert-butyl-2-thioimidazole

5-Benzyl-3-tert-Butyl-2-thiohydantoin (2.1 g, 0.008 mol) was dissolved in tetrahydrofuran (20 mL) under argon. A solution of lithium borohydride (4 mL of 2M LiBH$_4$ in THF, 0.008 mol) was added, and the resulting mixture was warmed to 50° C. Water (0.35 mL) was added dropwise. After 40 min, HPLC indicated that the reaction was complete. The reaction mixture was cooled to room temperature, acidified with 3M HCl (5 mL), diluted with water (50 mL), cooled to 0° C., and stirred for 30 min. A white solid was collected and air dried to give 1.4 g (71%) of 4-benzyl-1-tert-butyl-2-thioimidazole. HPLC analysis showed a purity of 93%. NMR (CDCl$_3$) δ 12.0 (s br, 1H), 7.4 (s, 5H), 6.5 (s, 1H), 3.9 (s, 2H), 1.9 (s, 9H).

Example 23

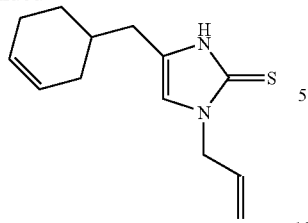

1-Allyl-4-(1,2,3,6-tetrahydrobenzyl)-2-thioimidazole

3-Allyl-5-(1,2,3,6-tetrahydrobenzylidene)-2-thiohydantoin (12.4 g, 0.05 mol) was dissolved in dioxane (50 mL). Lithium borohydride (0.7 g, 0.032 mol) was added, and the reaction mixture was cooled in a room temperature water bath. Water (3 mL) was added dropwise at such a rate to maintain the internal temperature between 50-60° C. After 20 min, lithium borohydride (0.7 g, 0.032 mol) and then water (3 mL) were added. During this addition, the reaction mixture was warmed to keep the internal temperature between 50-60° C. After 30 min, the last portion of lithium borohydride (0.7 g, 0.032 mol) was added. After an additional 30 min, HPLC analysis indicated that the reaction was complete. The reaction mixture was cooled in a room temperature water bath and acidified with acetic acid (10 mL) over 20 min. After a few minutes, 1M HCl (100 mL) was added. The color of the reaction mixture changed from red to yellow. The resulting mixture was heated at reflux for 2.5 hr, cooled to room temperature, and diluted with water (100 mL). The mixture was extracted with dichloromethane (2×75 mL). The combined organic layers were washed carefully with saturated sodium bicarbonate solution (2×50 mL), 1M HCl (1×50 mL), brine (1×50 mL), filtered through 1 PS filter paper and concentrated under reduced pressure to give 15 g of a brown-reddish oil that partially solidified. The oil was dissolved in methanol (25 mL). Water (20 mL) was added while the mixture was stirred with a stir-bar. After a few minutes, the resulting cloudy mixture was seeded with several crystals, and 25 mL of 25% methanol/water was added. After this suspension was stirred for 45 min at room temperature, the solid was collected and air dried to give 8.9 g (76%) of 1-allyl-4-(1,2,3,6-tetrahydrobenzyl)-2-thioimidazole with a purity of 90%. The solid was suspended over hexane (125 mL) and, while being stirred with a stir-bar, was heated at reflux for 15 min. The hexane layer was decanted, and this operation was repeated two more times. All three hexane layers were combined and placed in a hood over night. The resulting crystals were collected and dried to give 6.2 g (53%) of 1-allyl-4-(1,2,3,6-tetrahydrobenzyl)-2-thioimidazole as a tan solid. HPLC analysis showed a purity of 98%. NMR (CDCl$_3$) δ 13.5 (s br, 1H), 6.6 (s, 1H), 5.1-6.5 (m, 5H), 4.7 (two unresolved d, 2H), 2.5 (d br, 2H), 1.0-2.4 (m, 7H).

Example 24

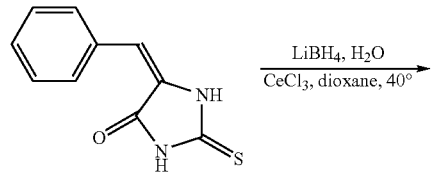

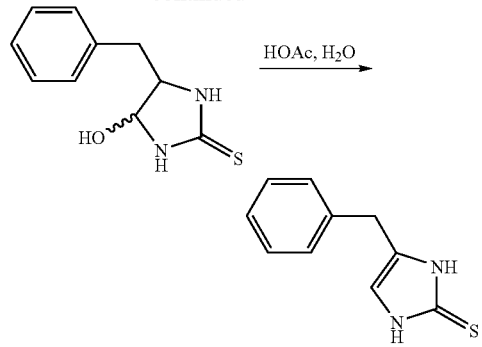

4-Benzyl-2-thioimidazole

A flask equipped with a magnetic stirrer and nitrogen atmosphere was charged with 0.22 g (0.010 mol) of LiBH$_4$ and 7 mL of dioxane. The suspension was stirred rapidly as 0.18 g (0.010 mol) of water was added dropwise. The flask was then immersed in a 40° C. bath for 15 min. After the mixture had cooled to room temperature, CeCl$_3$ (1.23 g, 0.0050 mol) was added. The mixture was stirred for 10 min, and then 5-benzylidenethiohydantoin (0.42 g, 0.0020 mol) in 5 mL of dioxane was added in 1 portion. After ca. 15 min, the flask was immersed in a 40° bath. After an additional 40 min, another 0.22 g (0.010 mol) of the borohydride was added. After a total of 65 min, this was followed by 0.11 g (0.0060 mol) of water. Finally, after an additional 15 min, another 0.11 g portion of water was added. After another 80 min, the mixture was slowly added to a rapidly stirring mixture of 3 g of acetic acid and 30 g of ice. The mixture was brought to a gentle boil for 10 min on a hotplate. The heat was turned off, and the pH was adjusted to >10 by the addition of potassium carbonate (causing formation of insoluble cerium carbonate). The mixture was stirred vigorously as it cooled to room temperature and for another ca. 14 hr. The solid was collected and washed with 2×5 mL of water. It was then resuspended in 30 mL of 10% aqueous acetic acid and stirred for 50 min. The solid was collected and washed with 2×5 mL of 10% acetic acid. After drying in a hood draft, the product weighed 0.22 g (58%). HPLC analysis of this material indicated about 95% purity. The major impurity was starting material. There was only trace, if any contamination with the over reduced substance (4-benzylimidazolidin-2-thione).

Example 25

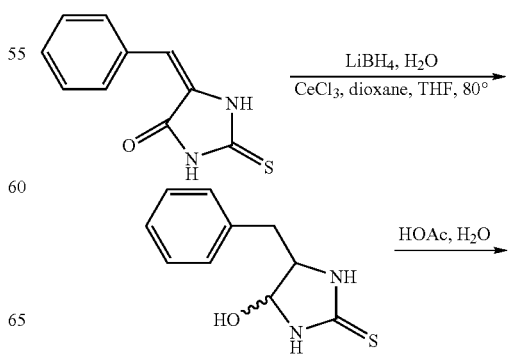

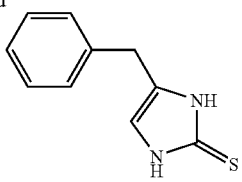

4-Benzyl-2-thioimidazole

A flask equipped with a magnetic stirrer and nitrogen atmosphere was charged with 0.16 g (0.0072 mol) of LiBH$_4$ and 3 mL of dioxane. The suspension was stirred rapidly as 0.61 g (0.0016 mol) of CeCl$_3$-7H$_2$O was added. The mixture was stirred for 2 hr, and then 5-benzylidenethiohydantoin (0.41 g, 0.0020 mol) in 3 mL of tetrahydrofuran (THF) and 1 mL of dioxane was added in 1 portion. The flask was immersed in an 80° bath for 5 min. The flask was withdrawn from the bath and allowed to cool. Then, 0.18 g (0.010 mol) of water was added. The flask was immersed in the bath for 2 min and withdrawn. An additional 0.37 g (0.001 mol) of CeCl$_3$-7H$_2$O was added. After the reaction flask was in the bath 10 min, an additional 0.077 g (0.0035 mol) LiBH$_4$ was added. After 10 min in the bath, HPLC analysis revealed that the intermediates, A, were 5.8 times the hydantoin, II, at 240 nm. The mixture was added dropwise to a rapidly stirred mixture of 3 g acetic acid and 30 g of ice. This mixture was heated to boiling for 10 min. As it cooled, The pH was adjusted to ca. 10 by addition of solid K$_2$CO$_3$. The solution was stirred overnight.

The resulting solid was collected, washed with 2×5 mL of water, resuspended in 30 mL of 10% aqueous acetic acid, and stirred at room temperature for about 20 hr. The solid was collected and washed with 3×5 mL of water. After drying, the product weighed 0.235 g (58%). HPLC analysis at 270 nm indicated a purity of 95%. The only other component present in significant quantity was the starting material.

Example 26

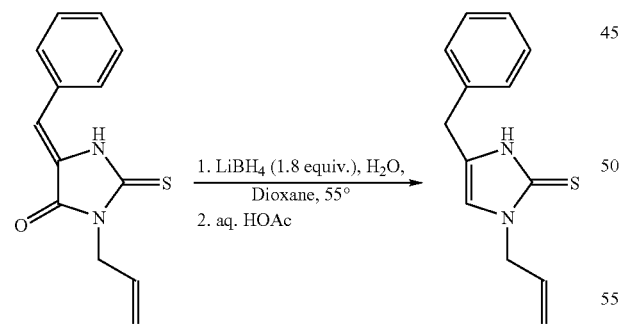

1-Allyl-4-benzyl-2-thioimidazole

3-Allyl-5-benzylidene-2-thiohydantoin (2.04 g, 0.0083 mol) was dissolved in 13 mL of dioxane in a flask equipped with a magnetic stirrer and nitrogen pressure. LiBH$_4$ (0.22 mol, 0.010 mol) was added in a single portion. The flask was immersed in a 55° bath, and 3×0.25 mL of water (total of 0.04 mol) were added at 5 min intervals. After ca. 5 min, the flask was removed from the bath and the progress was evaluated by HPLC. An additional 0.11 g (0.005 mol) of LiBH$_4$ was added, and the flask was again immersed in the bath for 5 min. After the mixture had cooled to room temperature, it was added dropwise to a rapidly stirring mixture of 1.5 g of acetic acid and 40 g of ice. The flask was washed with an additional 2 mL of dioxane. The mixture was diluted to 100 mL with water, and 1.2 M hydrochloric acid was used to bring the pH to 2. After the mixture had stirred for ca. 14 hr, the flask contained a large amount of freely suspended yellow solid and some darker material adhering to the stir bar. The latter was broken up with a glass rod, and the solid was collected and washed with water. After drying in a hood draft, the solid weighed 1.1 g (60%). HPLC analysis at 270 nm (near $\lambda_{max}$) was 93%. At 215 nm, reflecting a variety of impurity types, the purity was only 86%.

Example 27

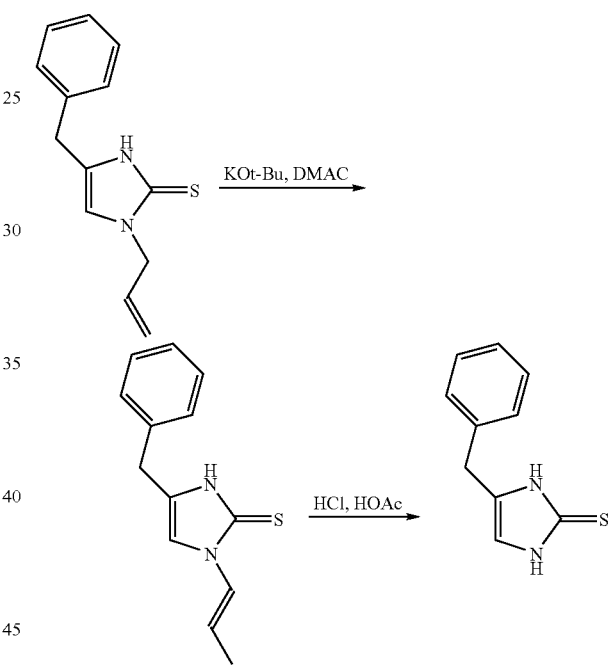

4-Benzyl-1-propenyl-2-thioimidazole

To a solution of 3-allyl-5-benzyl-2-thioimidazole (2.3 g, 0.01 mol) in dimethylacetamide (25 mL) was added potassium tert-butoxide (3.37 g, 0.03 mol) in one portion under argon. The color of the reaction mixture turned to green and finally to brown. The internal temperature went up to 35° C. The resulting mixture was heated on a steam bath for 20 min. HPLC analysis showed the reaction was complete. The reaction mixture was diluted with water (75 mL), cooled in an ice-water bath, acidified with acetic acid (2.5 mL) and stirred for 30 min. A tan solid was collected and dried to give 1.92 g (83%) of 4-Benzyl-1-propenyl-2-thioimidazole. HPLC analysis showed a purity of 99% for two isomers in a ratio of 95 to 5. NMR (CDCl$_3$) δ 12.0 (s br, 1H), 7.5 (s, 5H), 6.7-7.1 (m, 1H), 6.6 (s, 1H), 5.5-6.0 (m, 1H), 3.9 (two unresolved s, 2H), 1.6-1.8 (two d, 3H).

Example 28

4-Benzyl-2-thioimidazole

4-Benzyl-1-propenyl-2-thioimidazole (0.69 g, 0.003 mol) was dissolved in hot acetic acid (10 mL). 6M HCl (1 mL) was added, and the mixture was heated on a steam bath. HPLC after 15 min showed the reaction was complete. Water (10 mL) was added, and the mixture was extracted with dichloromethane (2×40 mL). The combined organic layers were washed with brine (1×25 mL), filtered through 1 PS filter paper and concentrated under reduced pressure at 50° C. to give an oil. The oil was triturated with dichloromethane (10 mL). The resulting tan solid was collected and air dried to give 0.18 g (32%) of 4-benzyl-2-thioimidazole. HPLC analysis showed a purity of 99%. NMR (CDCl$_3$:d$_6$-DMSO) δ 12.5 (s br, 2H), 7.5 (s, 5H), 6.5 (s, 1H), 3.9 (s, 2H).

Example 29

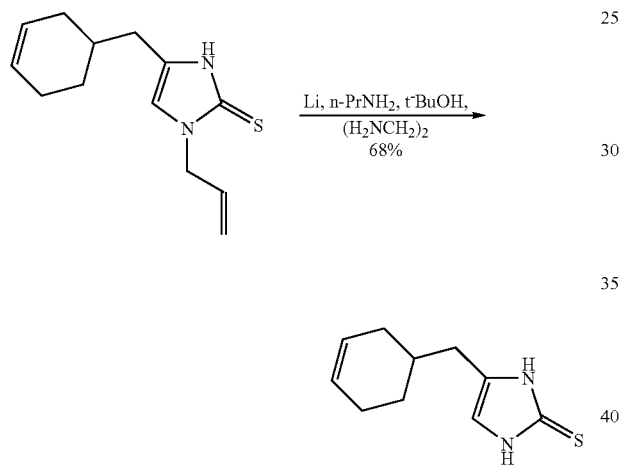

4-(1,2,3,6-Tetrahydrobenzyl)-2-thioimidazole

To a solution of 1-Allyl-4-(1,2,3,6-tetrahydrobenzyl)-2-thioimidazole (1.42 g, 0.006 mol) in n-propylamine (30 mL) at −10° C. was added ethylenediamine (1.44 g, 0.024 mol) and tert-butanol (2.22 g, 0.03 mol). Lithium wire (0.21 g, 0.03) was added in small pieces. After 5 min. the internal temperature went up to −3° C. and then went down to −10° C. After 30 min stirring at −10° C., lithium wire (0.21 g, 0.03 mol) was added in small pieces. After 30 min a blue color persisted, and HPLC showed that the reaction was complete. The solution was decanted from unreacted lithium (unreacted lithium after washing with hexane weighed 0.1 g) and concentrated under reduced pressure. To the residue was added 25 g crushed ice, 25 mL water and 3M HCl (25 mL). After 15 min stirring, a white solid was collected, washed well with cold water and air dried to give 0.94 g (81%) of 4-(1,2,3,6-tetrahydrobenzyl)-2-thioimidazole. HPLC analysis showed a purity of 93%. NMR (CD$_3$OD) δ 6.7 (s, 1H), 5.7 (s br, 2H), 4.8 (s br, 2H), 1.5-2.6 (m, 9H).

Example 30

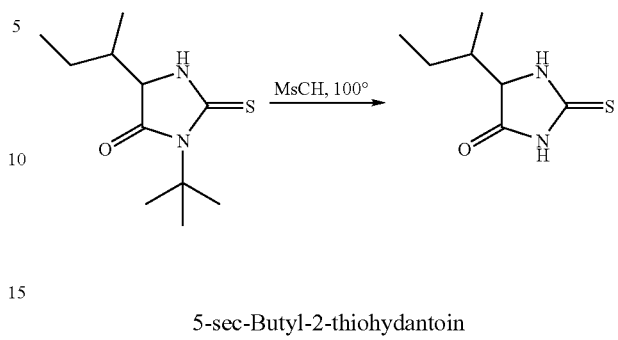

5-sec-Butyl-2-thiohydantoin 5-sec-Butyl-3-tert-butyl-2-thiohydantoin (1.35 g, 0.006 mol) was suspended over methanesulfonic acid (5 mL) and heated at 100° C. under argon. HPLC analysis after 1.5 hr showed the reaction was complete. The reaction mixture was cooled to room temperature, diluted with dichloromethane (100 mL), washed with brine (2×50 mL), filtered through 1 PS filter paper and concentrated under reduced pressure to give 1.3 g of an oil. The oil was chromatographed on a 25 g flash chromatography silica gel with 10 g of anhydrous sodium sulfate on top. The column was eluted with 50 mL portions of 25% dichloromethane in hexane for fractions 1-4, 50% dichloromethane in hexane for fractions 5-7, 75% dichloromethane in hexane for fractions 8-9, dichloromethane for fractions 10-11 and 25% ethyl acetate in hexane for fractions 12-16. The product was eluted in fractions 12-14 (TLC solvent: 50% ethyl acetate in hexane) to give 0.7 g (70%) of 5-sec-Butyl-2-thiohydantoin as a colorless oil which solidified. HPLC analysis showed a purity of 98%. NMR (CDCl$_3$:CD$_3$OD) δ 4.9 (s br, 2H), 4.4 (t br, 1H), 0.7-1.8 (m, 9H).

Example 31

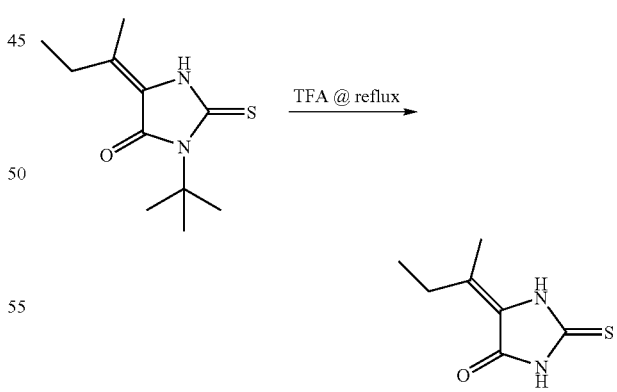

5-sec-Butylidene-2-thiohydantoin 5-sec-Butylidene-3-tert-butyl-2-thiohydantoin (0.34 g, 0.0015 mol) was dissolved in trifluoroacetic acid (5 mL) and heated at reflux for 2 hr. At this time HPLC analysis showed the reaction was complete. The reaction mixture was diluted with dichloromethane (50 mL) and washed with water (2×25 mL), saturated sodium bicarbonate (1×25 mL), brine (1×25 mL). The mixture was filtered through 1 PS filter paper and concentrated under reduced pressure to give 0.2 g of a yellow solid. The solid was triturated with hexane (5 mL) and placed in a freezer over the weekend. The solid was collected and dried to give 0.18 g (70%) of 5-sec-butylidene-2-thiohydantoin. HPLC analysis showed a purity of 99%. NMR (CD$_3$OD) δ 4.8 (s br, 2H), 2.0-3.2 (m, 5H), 1.2 (two unresolved t, 3H).

Example 32

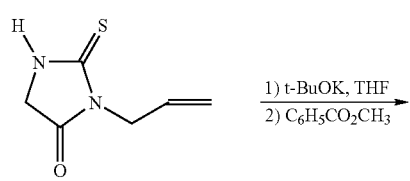

3-Allyl-5-benzoyl-2-thiohydantoin

To a solution of 3-allyl-2-thiohydantoin (1.56 g, 0.01 mol) in tetrahydrofuran (50 mL) was added a solution of 1M potassium tert-butoxide in tetrahydrofuran (12 mL, 0.012 mol) in one portion under argon. A red solid formed. Then methyl benzoate (1.7 g, 0.0125 mol) was added to the reaction mixture. The resulting mixture was stirred and heated at reflux for 5.5 hr and at room temperature overnight. The reaction mixture was diluted with water (50 mL) and 6M hydrochloric acid (50 mL) and then was then extracted with dichloromethane (2×50 mL). The combined organic layers were washed with brine (1×50 mL), filtered through 1 PS filter paper and concentrated under reduced pressure to give 3.2 g of dark brown oil. The oil was flash chromatographed on a 50 g flash chromatography silica gel with 10 g of anhydrous sodium sulfate on top. The column was eluted with 50 mL portions of 10% ethyl acetate in hexane for fractions 1-4 and 15% ethyl acetate in hexane for fractions 5-10. The product was eluted in fractions 6-9 (TLC solvent: 50% ethyl acetate/hexane) to give 1.2 g (46%) of 3-allyl-5-benzoyl-2-thiohydantoin as yellow needles. The material was 97% pure by HPLC. NMR (CDCl$_3$) δ 11.2 (s br, 1H), 10.1 (s br, 1H), 7.5-8.1 (m, 5H), 5.1-6.3 (m, 3H), 4.6 (d, 2H).

X-ray crystallography of 3-allyl-5-benzoyl-2-thiohydantoin indicated that, this compound exist in the crystal as a dimer with the following structure:

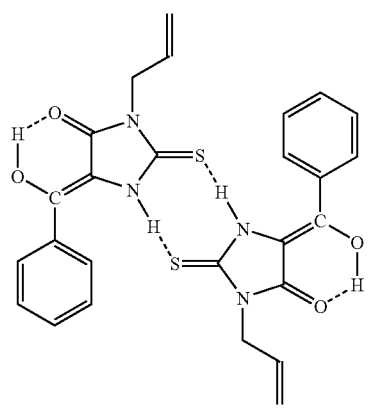

Example 33

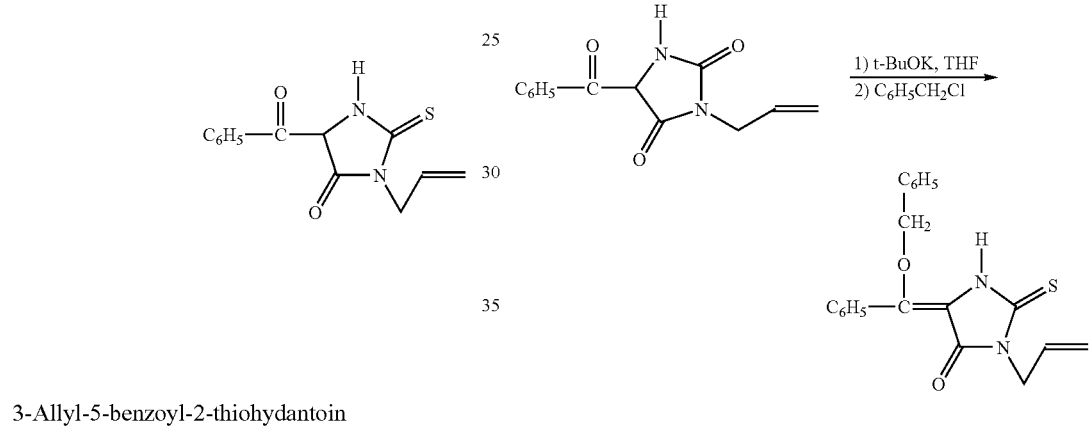

5-[Phenyl(phenylmethoxy)methylene]-3-allyl-2-thiohydantoin

To a solution of 3-allyl-5-benzoyl-2-thiohydantoin (0.098 g, 0.0003 mol) and benzyl chloride (0.042 g, 0.00033 mol) in tetrahydrofuran (2 mL) was added a solution of 1M potassium tert-butoxide in tetrahydrofuran (0.33 mL, 0.00033 mol) under argon. A cherry solid was formed in the reaction mixture. The resulting mixture was heated at reflux for 1 hr and then cooled to room temperature. The reaction mixture was diluted with ethyl acetate (40 mL), washed with 3M HCl (2×20 mL) and brine (1×20 mL), filtered through 1 PS filter paper and concentrated under reduced pressure to give 0.13 g of a brown oil which solidified on standing. This solid was triturated with hexane (5 mL) once and then was dried under high vacuum. NMR (CDCl$_3$) δ (10.9 s br, 1H), 8.6-8.9 (m, 2H), 7.3-7.9 (m, 8H), 4.7 (S, 2H), 4.4 (d, 2H).

While particular embodiments of the invention have been described it will be understood of course that the invention is not limited thereto since many obvious modifications can be made and it is intended to include within this invention any such modifications as will fall within the scope of the appended claims.

The invention claimed is:

1. A method of making a 4-substituted-2-thioimidazole which comprises the step of reducing a 5-substituted-2-thiohydantoin to a 4-substituted-2-imidazole-2-thione, wherein said 5-substituted-2-thiohydantoin has a formula

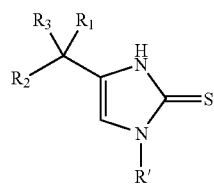

and wherein the 4-substituted-2-thioimidazole has a formula

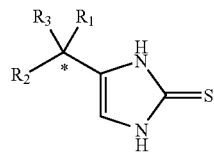

wherein R', $R_1$, $R_2$ and $R_3$ are independently selected from the group consisting of H, hydrocarbyl and substituted hydrocarbyl, and wherein the carbon atom marked with a star is a chiral carbon atom.

2. The method of claim 1 wherein R', $R_1$, $R_2$ and $R_3$ are independently selected from the group consisting of H, alkyl, alkenyl, aryl and alkaryl.

3. The method of claim 1 wherein R', $R_1$, $R_2$ and $R_3$ are independently selected from the group consisting of H, $C_1$ to $C_7$ alkyl, $C_2$ to $C_7$ alkenyl and lower alkaryl.

4. The method of claim 1 wherein R', $R_1$, $R_2$ and $R_3$ are independently selected from the group consisting of H, $C_1$ to $C_7$ alkyl, $C_2$ to $C_7$ alkenyl and carbocyclic aryl having one ring and lower alkyl carbocylic aryl having one ring.

5. The method of claim 1 wherein R', $R_1$, $R_2$ and $R_3$ are independently selected from the group consisting of H, $C_1$ to $C_7$ alkyl, $C_2$ to $C_7$ alkenyl and lower alkyl carbocyclic aryl having one ring.

6. The method of claim 5 wherein R', $R_1$, $R_2$ and $R_3$ are unsubstituted.

7. The method of claim 6 wherein $R_1$, $R_2$, and $R_3$ are independently selected from the group consisting of 1-1, $CH_3$, $C_2H_5$, cyclohexenyl and phenyl.

8. The method of claim 1 wherein R' is selected from the group consisting of H, $CH_2CHCH_2$, $(CH_3)_3C$ and p-methoxybenzyl.

* * * * *